United States Patent
Fallin et al.

(10) Patent No.: US 11,259,817 B2
(45) Date of Patent: Mar. 1, 2022

(54) FREEFORM TRI-PLANAR OSTEOTOMY GUIDE AND METHOD

(71) Applicant: CROSSROADS EXTREMITY SYSTEMS, LLC, Memphis, TN (US)

(72) Inventors: T. Wade Fallin, Hyde Park, UT (US); Robert W. Hoy, Essex Junction, VT (US); Daniel J. Triplett, Providence, UT (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 0 days.

(21) Appl. No.: 17/348,083

(22) Filed: Jun. 15, 2021

(65) Prior Publication Data

US 2021/0307763 A1 Oct. 7, 2021

Related U.S. Application Data

(63) Continuation of application No. 16/680,467, filed on Nov. 11, 2019, which is a continuation of application No. 16/205,968, filed on Nov. 30, 2018, now Pat. No. 10,470,779, which is a continuation of application No. 14/959,354, filed on Dec. 4, 2015, now Pat. No. 10,292,713.

(60) Provisional application No. 62/108,936, filed on Jan. 28, 2015.

(51) Int. Cl.
*A61F 5/00* (2006.01)
*A61B 17/15* (2006.01)

(52) U.S. Cl.
CPC .................. *A61B 17/151* (2013.01)

(58) Field of Classification Search
CPC combination set(s) only.
See application file for complete search history.

(56) References Cited

U.S. PATENT DOCUMENTS

| | | |
|---|---|---|
| 4,069,824 A | 1/1978 | Weinstock |
| 4,335,715 A | 6/1982 | Kirkley |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,627,425 A | 12/1986 | Reese |
| 4,632,102 A | 12/1986 | Comparetto |

(Continued)

FOREIGN PATENT DOCUMENTS

| | | |
|---|---|---|
| EP | 0 570 187 | 11/1993 |
| EP | 0 570 187 | 7/1996 |

(Continued)

OTHER PUBLICATIONS

Accu-Cut Osteotomy Guide System, BioPro Implants, www.bioproimplants.com, Brochure No. 17136, Rev4, 2 pp.

(Continued)

*Primary Examiner* — Sameh R Boles
(74) *Attorney, Agent, or Firm* — Knobbe, Martens, Olson & Bear, LLP

(57) ABSTRACT

Systems and methods for performing an osteotomy are presented. Examples include forming a fusion osteotomy at a metatarsocuneiform joint of the first ray of a human foot.

16 Claims, 26 Drawing Sheets

(56) References Cited

U.S. PATENT DOCUMENTS

| | | | |
|---|---|---|---|
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,757,810 A | 7/1988 | Reese |
| 4,952,214 A | 8/1990 | Comparetto |
| 4,959,066 A | 9/1990 | Dunn et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann |
| 5,078,719 A | 1/1992 | Schreiber |
| 5,112,334 A | 5/1992 | Alchermes |
| 5,147,364 A | 9/1992 | Comparetto |
| 5,176,685 A | 1/1993 | Rayhack |
| 5,246,444 A | 9/1993 | Schreiber |
| 5,413,579 A | 5/1995 | Du Toit |
| 5,449,360 A | 9/1995 | Schreiber |
| 5,470,335 A | 11/1995 | Du Toit |
| 5,540,695 A | 7/1996 | Levy |
| 5,578,038 A | 11/1996 | Slocum |
| 5,601,565 A | 2/1997 | Huebner |
| 5,613,969 A | 3/1997 | Jenkins, Jr. |
| 5,620,448 A | 4/1997 | Puddu |
| 5,643,270 A | 7/1997 | Combs |
| 5,667,510 A | 9/1997 | Combs |
| 5,722,978 A | 3/1998 | Jenkins |
| 5,749,875 A | 5/1998 | Puddu |
| 5,779,709 A | 7/1998 | Harris, Jr. |
| 5,843,085 A | 12/1998 | Graser |
| 5,911,724 A | 6/1999 | Wehrli |
| 5,980,526 A | 11/1999 | Johnson |
| 5,984,931 A | 11/1999 | Greenfield |
| 6,007,535 A | 12/1999 | Rayhack |
| 6,027,504 A | 2/2000 | McGuire |
| 6,030,391 A | 2/2000 | Brainard |
| 6,203,545 B1 | 3/2001 | Stoffella |
| 6,248,109 B1 | 6/2001 | Stoffella |
| 6,391,031 B1 | 5/2002 | Toomey |
| 6,547,793 B1 | 4/2003 | McGuire |
| 6,676,662 B1 | 1/2004 | Bagga |
| 6,755,838 B2 | 6/2004 | Trnka |
| 6,796,986 B2 | 9/2004 | Duffner |
| 7,018,383 B2 | 3/2006 | McGuire |
| 7,112,204 B2 | 9/2006 | Justin |
| 7,182,766 B1 | 2/2007 | Mogul |
| 7,540,874 B2 | 6/2009 | Trumble |
| 7,572,258 B2 | 8/2009 | Stiernborg |
| 7,691,108 B2 | 4/2010 | Lavallee |
| 7,763,026 B2 | 7/2010 | Egger |
| 7,967,823 B2 | 6/2011 | Ammann |
| 7,972,338 B2 | 7/2011 | O'Brien |
| 8,062,301 B2 | 11/2011 | Ammann |
| 8,083,746 B2 | 12/2011 | Novak |
| 8,137,406 B2 | 3/2012 | Novak |
| 8,236,000 B2 | 8/2012 | Ammann |
| 8,262,664 B2 | 9/2012 | Justin |
| 8,277,459 B2 | 10/2012 | Sand |
| 8,282,645 B2 | 10/2012 | Lawrence et al. |
| 8,409,209 B2 | 4/2013 | Ammann |
| 8,496,662 B2 | 7/2013 | Novak |
| 8,529,571 B2 | 9/2013 | Horan |
| 8,540,777 B2 | 9/2013 | Ammann |
| 8,545,508 B2 | 10/2013 | Collazo |
| D695,402 S | 12/2013 | Dacosta et al. |
| 8,652,142 B2 | 2/2014 | Geissler |
| 8,657,820 B2 | 2/2014 | Kubiak |
| 8,702,715 B2 | 4/2014 | Ammann |
| 8,771,279 B2 | 7/2014 | Philippon |
| 8,777,948 B2 | 7/2014 | Bernsteiner |
| 8,888,785 B2 | 11/2014 | Ammann |
| 8,900,247 B2 | 12/2014 | Tseng |
| 8,906,026 B2 | 12/2014 | Ammann |
| 9,113,920 B2 | 8/2015 | Amman |
| 9,687,250 B2 | 6/2017 | Dayton et al. |
| 10,292,713 B2 | 5/2019 | Fallin et al. |
| 10,470,779 B2 | 11/2019 | Fallin et al. |
| 2002/0165552 A1 | 11/2002 | Duffner |
| 2004/0097946 A1 | 5/2004 | Dietzel |
| 2004/0138669 A1 | 7/2004 | Horn |
| 2005/0070909 A1 | 3/2005 | Egger |
| 2005/0251147 A1 | 11/2005 | Novak |
| 2005/0273112 A1 | 12/2005 | McNamara |
| 2006/0129163 A1 | 6/2006 | McGuire |
| 2006/0264961 A1 | 11/2006 | Murray |
| 2007/0010818 A1 | 1/2007 | Stone |
| 2007/0265634 A1 | 11/2007 | Weinstein |
| 2007/0276383 A1 | 11/2007 | Rayhack |
| 2008/0015603 A1 | 1/2008 | Collazo |
| 2008/0039850 A1 | 2/2008 | Rowley |
| 2008/0147073 A1 | 6/2008 | Ammann |
| 2008/0195215 A1 | 8/2008 | Morton |
| 2008/0269908 A1 | 10/2008 | Warburton |
| 2009/0036931 A1 | 2/2009 | Pech |
| 2009/0054899 A1 | 2/2009 | Ammann |
| 2009/0222047 A1 | 9/2009 | Graham |
| 2010/0130981 A1 | 5/2010 | Richards |
| 2011/0178524 A1 | 7/2011 | Lawrence |
| 2011/0188550 A1 | 8/2011 | Orbay |
| 2012/0016426 A1 | 1/2012 | Robinson |
| 2012/0185056 A1 | 7/2012 | Warburton |
| 2012/0191199 A1 | 7/2012 | Raemisch |
| 2012/0303033 A1* | 11/2012 | Weiner ............... A61B 17/8061 606/87 |
| 2013/0012949 A1 | 1/2013 | Fallin |
| 2013/0172942 A1 | 7/2013 | Lewis et al. |
| 2013/0226248 A1 | 8/2013 | Hatch |
| 2013/0226252 A1 | 8/2013 | Mayer |
| 2013/0331845 A1 | 12/2013 | Horan |
| 2014/0188139 A1 | 7/2014 | Fallin |
| 2014/0194999 A1 | 7/2014 | Orbay |
| 2014/0343555 A1 | 11/2014 | Russi |
| 2015/0057667 A1 | 2/2015 | Ammann |
| 2015/0245858 A1 | 9/2015 | Ammann |
| 2016/0015426 A1 | 1/2016 | Dayton |
| 2016/0192950 A1 | 7/2016 | Dayton et al. |
| 2016/0324532 A1 | 11/2016 | Montoya et al. |
| 2017/0042598 A1 | 2/2017 | Santruck et al. |
| 2017/0042599 A1 | 2/2017 | Bays et al. |
| 2017/0164989 A1 | 6/2017 | Weiner et al. |
| 2020/0078025 A1 | 3/2020 | Fallin et al. |

FOREIGN PATENT DOCUMENTS

| | | |
|---|---|---|
| WO | WO 00/006036 | 2/2000 |
| WO | WO 04/075775 | 9/2004 |
| WO | WO 04/089227 | 10/2004 |
| WO | WO 05/041785 | 5/2005 |
| WO | WO 07/008348 | 1/2007 |
| WO | WO 08/097781 | 8/2008 |
| WO | WO 16/134154 | 8/2016 |
| WO | WO 16/134160 | 8/2016 |

OTHER PUBLICATIONS

Arthrex Hallux Valgus Solutions, Arthrex, Inc., www.arthrex.com 2009, 2 pp.

Comprehensive Solutions for Forefoot and Midfood Surgery using the Mini TightRope System, Arthrex, Inc., www.arthrex.com 2012, 15 pp.

DiDomenico, Lawrence A., et al. "Lapidus Bunionectomy: First Metatarsal-Cuneiform Arthrodesis," Souhterland, Chapter 31, Aug. 18, 2012.

Distal Extremities Orthopaedic Update, Arthrex, Inc., www.arthrex.com, 2014, 24 pp.

Dobbe, et al., "Computer-Assisted and Patient-Specific 3-D Planning and Evaluation of a Single-Cut Rotational Osteotomy for Complex Long-Bone Deformities", Med Biol Eng Comput (2011) 49:1363-1370.

Foot & Ankle Repair and Reconstruction Technology, Arthrex GmbH, www.arthrex.com, 2016, 86 pp.

(56) References Cited

OTHER PUBLICATIONS

Gregg, Julie, et al., "Plantar Plate Repair and Weil Osteotomy for Meteatarsophalangeal Joint Instability", Foot and Ankie Surgery 13(2007) 116-121.
Meyer, D.C., et al., "A New Methodology for the Planning of Single-Cut Corrective Osteotomies of Mal-Aligned Long Bones", Clinical Biomechanics 20(2005) 223-227.
Oscillating Saw Attachment for EPD/APD, Colibri II and Small Electric Drive, Synthes GmbH, www.synthes.com, 2012, 2 pp.
Scarf Osteotomy Technical Information Sheet, TALUS group of GECO, www.geco-medical.org, 2004, 2 pp.
Shurnas, Paul S., M.D., et al., Proximal Metatarsal Opening Wedge Osteotomy: PMOW—Arthrex LPS System, Arthrex, Inc., www.arthrex.com, 2008, 1 pp.
Speed Triad Medial Technique, BioMedical Enterprises, www.bme-tx.com, 2015, 2 pp.
The Accu-Cut Osteotomy Guide System, BioPro Implants, www.bioproimplants.com, Brochure No. 16932 Rev07, 2 pp.
The Next Generation in Foot & Ankle Repair and Reconstruction Technology, Arthrex, Inc., www.arthrex.com, 2016, 76 pp.
The Next Generation in Foot & Ankle Repair and Reconstructions Technology, Arthrex, Inc., www.arthrex.com, 72 pp.
Weil, Lowell Jr., et al., "Anatomic Plantar Plate Repair Using the Weil Metatarsal Osteotomy Approach", Foot & Ankle Specialist, http://fas.sagepub.com/, 2011, 7 pp.

\* cited by examiner

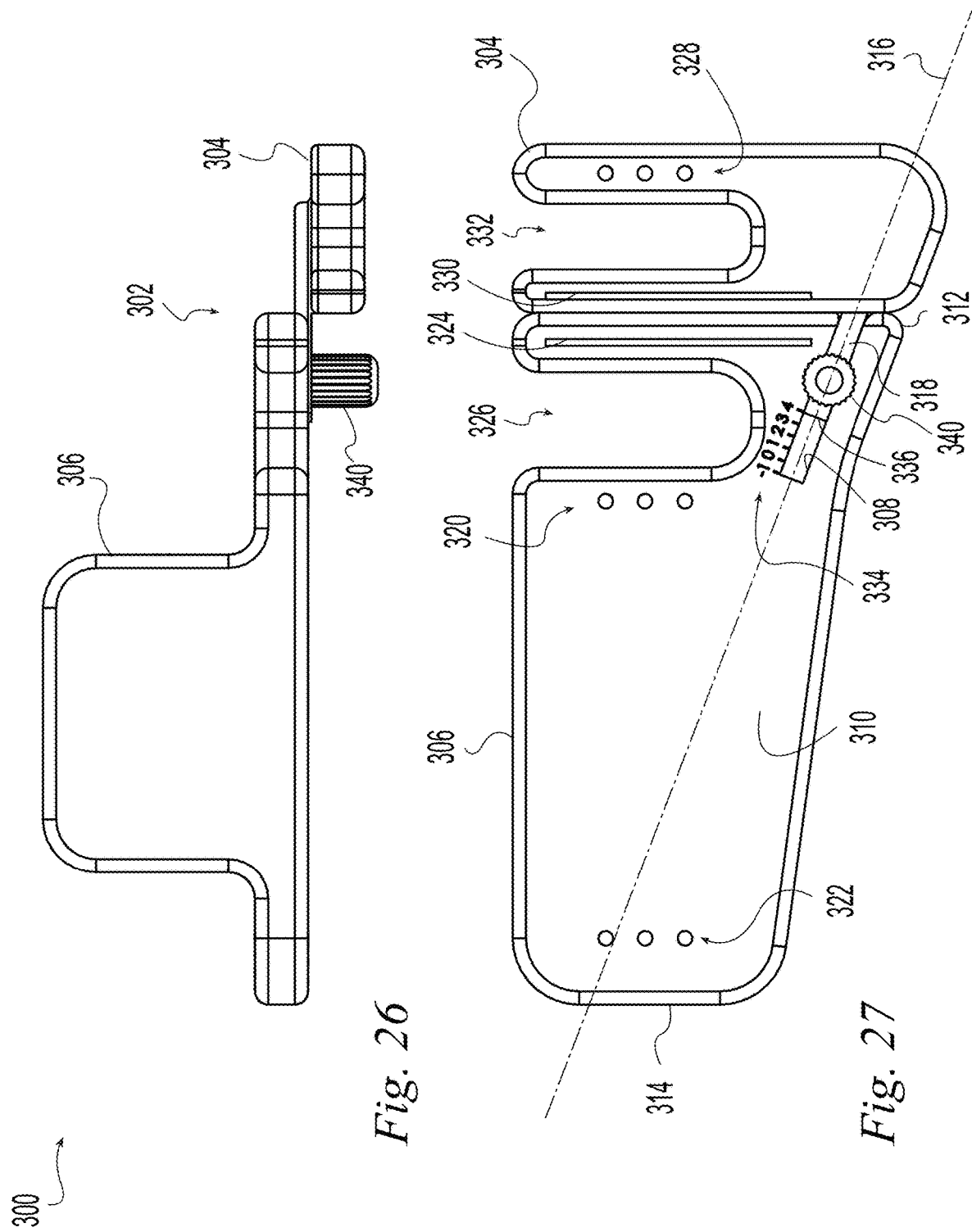

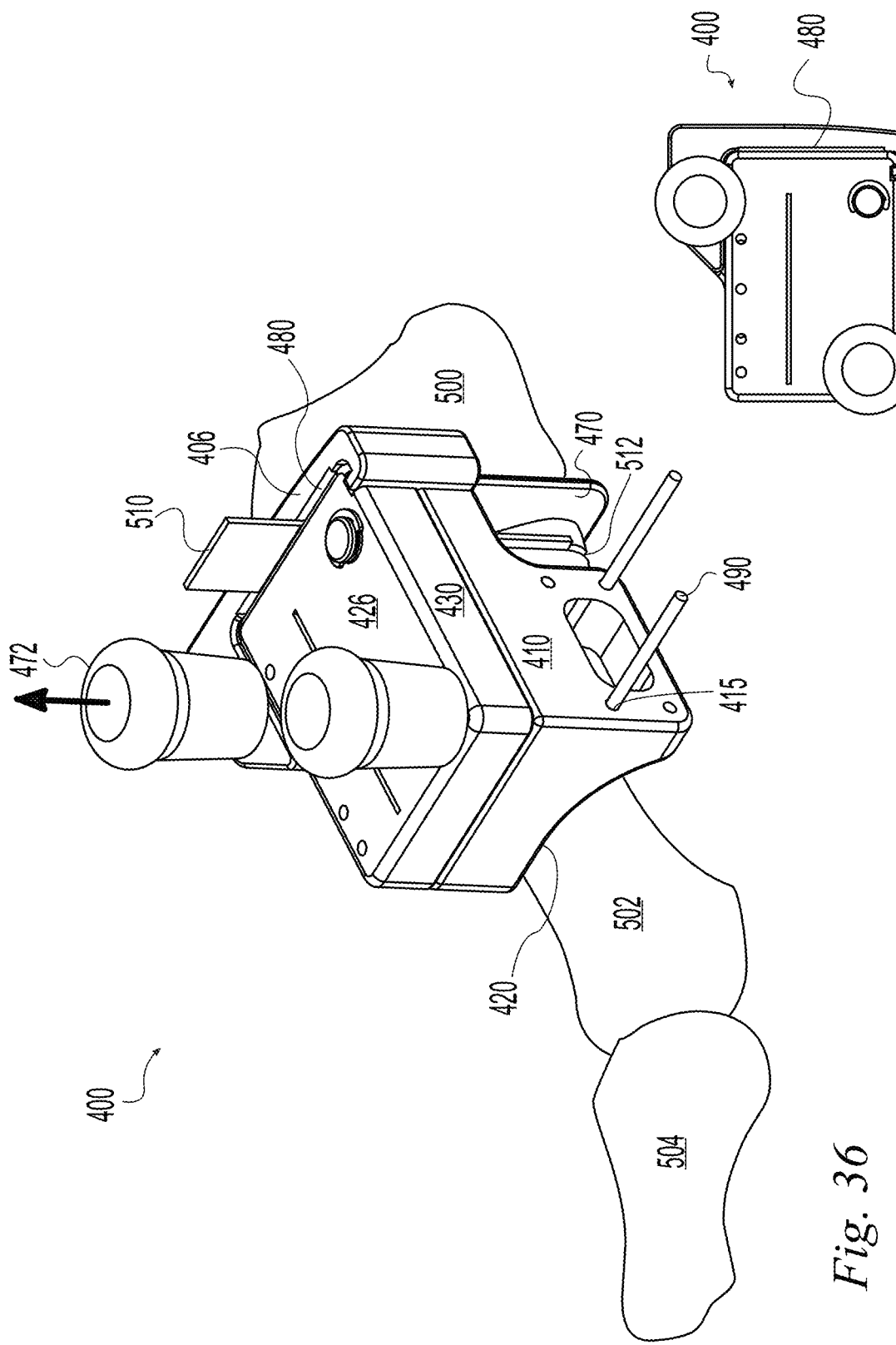

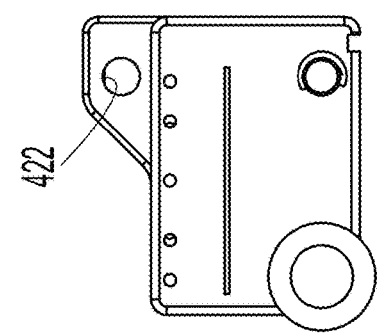
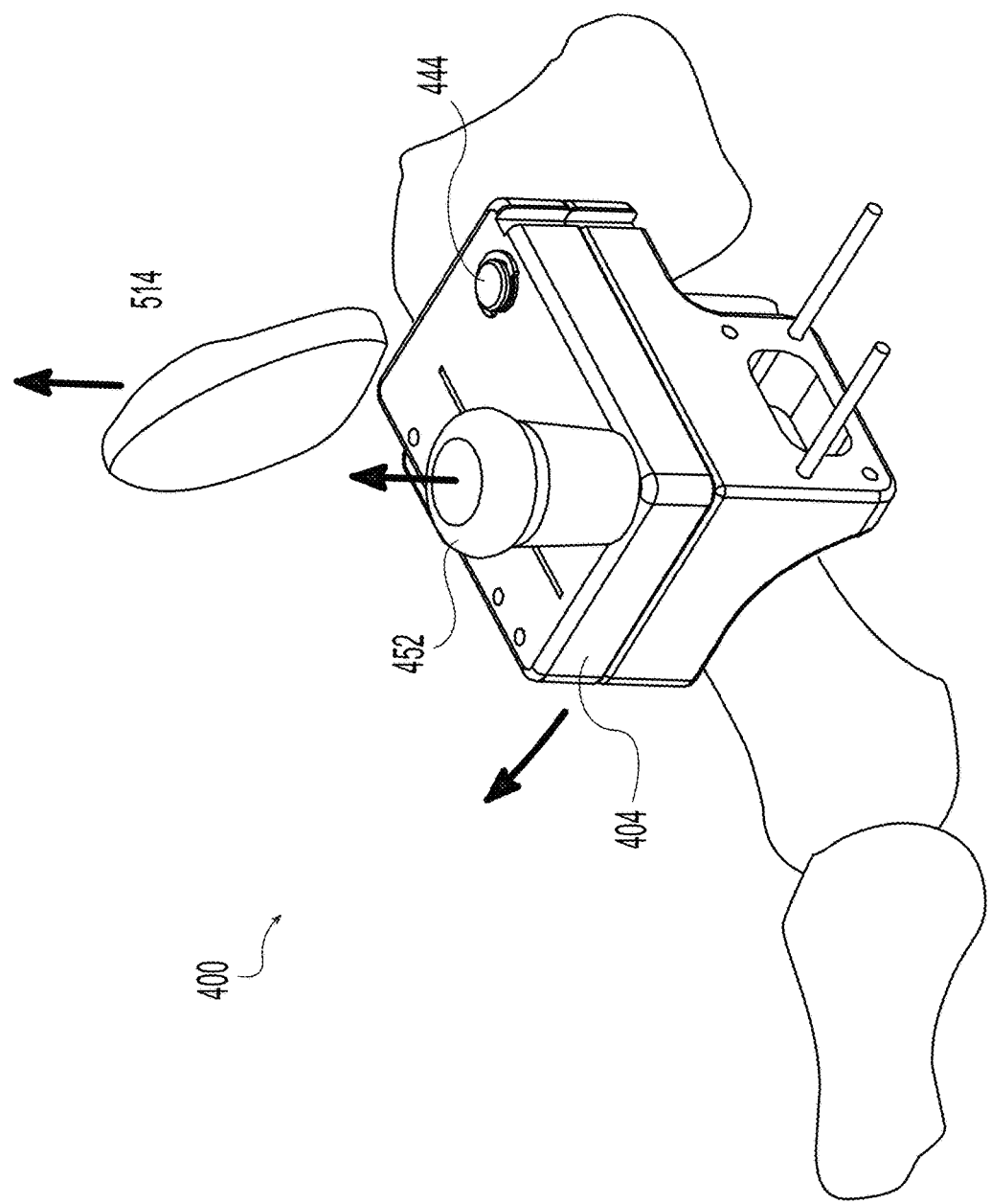

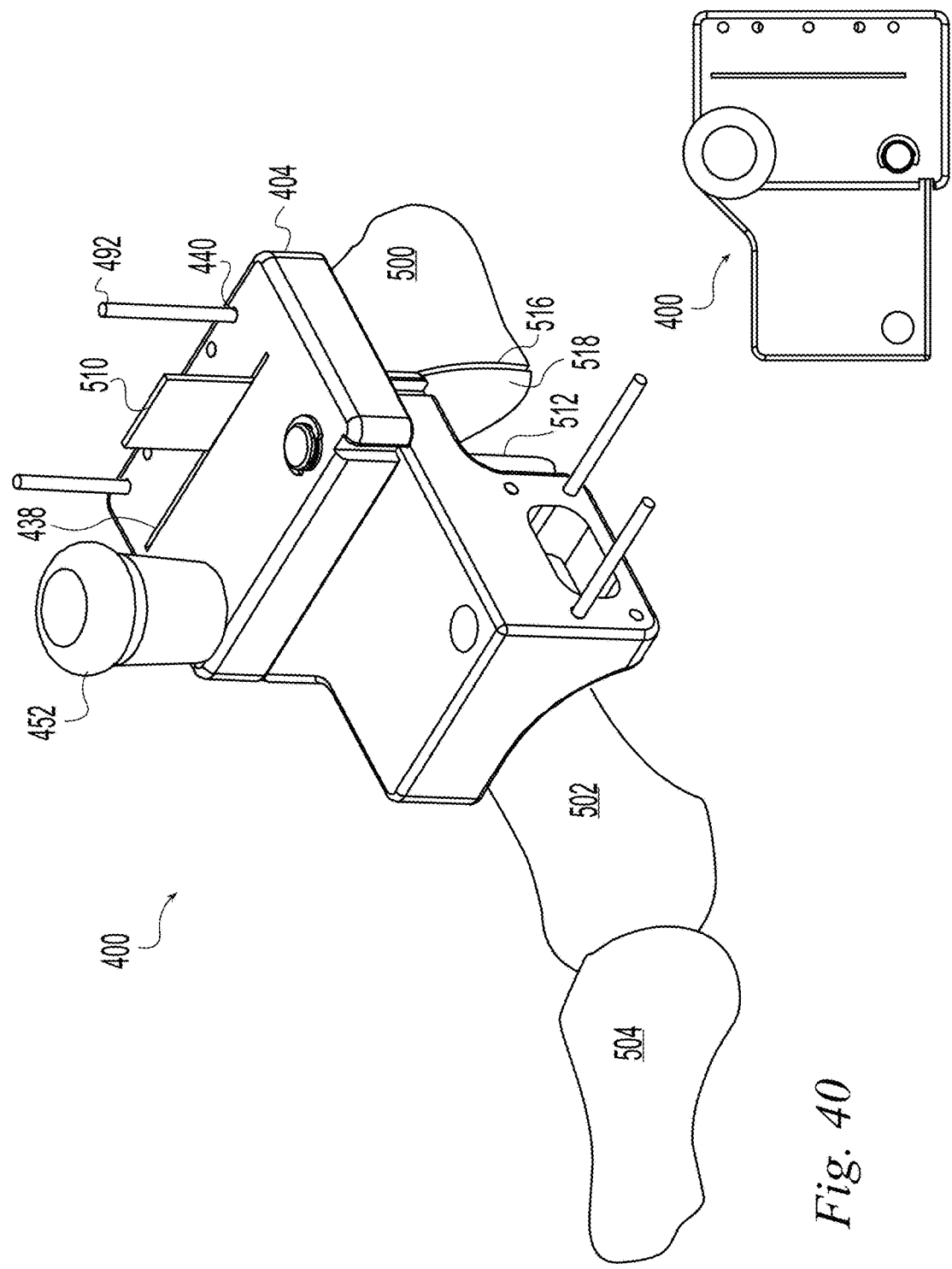

FREEFORM TRI-PLANAR OSTEOTOMY GUIDE AND METHOD

CROSS-REFERENCE TO RELATED APPLICATIONS

This application is a continuation of U.S. patent application Ser. No. 16/680,467, filed Nov. 11, 2019, entitled FREEFORM TRI-PLANAR OSTEOTOMY GUIDE AND METHOD, which is a continuation of U.S. patent application Ser. No. 16/205,968, filed Nov. 30, 2018, now U.S. Pat. No. 10,470,779 entitled FREEFORM TRI-PLANAR OSTEOTOMY GUIDE AND METHOD, which is a continuation of U.S. patent application Ser. No. 14/959,354, filed Dec. 4, 2015, now U.S. Pat. No. 10,292,713, entitled FREEFORM TRI-PLANAR OSTEOTOMY GUIDE AND METHOD, which claims the benefit of U.S. Provisional Application No. 62/108,936, filed Jan. 28, 2015, entitled FREEFORM TRI-PLANAR OSTEOTOMY GUIDE AND METHOD, which are incorporated herein by reference as though set forth in their entirety.

FIELD

The invention relates to methods, implants, and instruments for performing an osteotomy.

BACKGROUND

Various conditions may affect skeletal joints such as the deterioration, elongation, shortening, or rupture of soft tissues, cartilage, and/or bone associated with the joint and consequent laxity, pain, and/or deformity. It is often desirable to change the angular alignment of a bone or a portion of a bone to restore function and/or reduce pain. To this end, various osteotomy procedures and instruments have been proposed. For example, osteotomies have been performed throughout the body to make various angular adjustments such as in a tibia, fibula, femur, pelvis, humerus, ulna, radius, metacarpal, metatarsal, and other bones. In some cases it is desirable to induce the fusion of a skeletal joint, i.e. an arthrodesis, in a predetermined position. The present invention provides improved osteotomy and arthrodesis methods, implants, and instruments.

SUMMARY

The present invention provides systems and methods for performing an osteotomy. An osteotomy system may facilitate performance of an osteotomy between a metatarsus and a cuneiform defining a metatarsocuneiform joint of a human foot.

In one aspect of the invention, the osteotomy system may include an osteotomy guide with a joint alignment feature that facilitates alignment of the osteotomy guide with the metatarsocuneiform joint via insertion of an element into the metatarsocuneiform joint, one or more fixation elements that facilitate fixation of the osteotomy guide to at least one of the metatarsus and the cuneiform, and a first guide feature spaced apart from the joint alignment feature. With the osteotomy guide positioned to align the joint alignment feature with the metatarsocuneiform joint, the first guide feature may be positioned to guide a first cutter to cut the metatarsus to remove part of the metatarsus.

In another aspect of the invention, the osteotomy system may include an osteotomy guide with a first guide feature positionable to guide a first cutter to cut the metatarsus to remove part of the metatarsus, and a second guide feature that, with first guide feature positioned to guide the first cutter to cut the metatarsus, is positioned to guide one of the first cutter and a second cutter to remove part of the cuneiform to create a gap between the metatarsus and the cuneiform. The first guide feature and the second guide feature may be on a one-piece guide body.

In another aspect of the invention, the osteotomy system may include an osteotomy guide with a first guide feature that is positionable to guide a first cutter to cut the metatarsus to remove part of the metatarsus, and a second guide feature that, with the first guide feature unobstructed and positioned to guide the first cutter to cut the metatarsus, is positioned to guide one of the first cutter and a second cutter to remove part of the cuneiform to create a gap between the metatarsus and the cuneiform.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 26 is a top plan view of an osteotomy guide like that of FIG. 14 having a two-piece construction;

FIG. 27 is a side elevation view of the osteotomy guide of FIG. 26;

FIGS. 36-41 illustrate the use of the osteotomy guide of FIG. 33 to perform an osteotomy.

DETAILED DESCRIPTION OF THE PREFERRED EMBODIMENT

The following illustrative examples describe implants, instruments and techniques for performing an osteotomy. The present invention may be used to perform osteotomies on any bone including but not limited to a tibia, fibula, femur, pelvis, humerus, ulna, radius, metacarpal, and metatarsal. The invention may be used to perform an osteotomy between two portions of the same bone or between two different bones at a joint to e.g. perform an arthrodesis. For example, the present invention may be used to perform an arthrodesis at any joint such as at the hip, knee, ankle, wrist, elbow, between adjacent bones in the hands and feet, between spinal vertebrae, or between any other bones. However, for convenience, the invention will be illustrated with reference to a metatarsus and cuneiform at a metatarsocuneiform joint of the first ray of a human foot.

Figure 1:
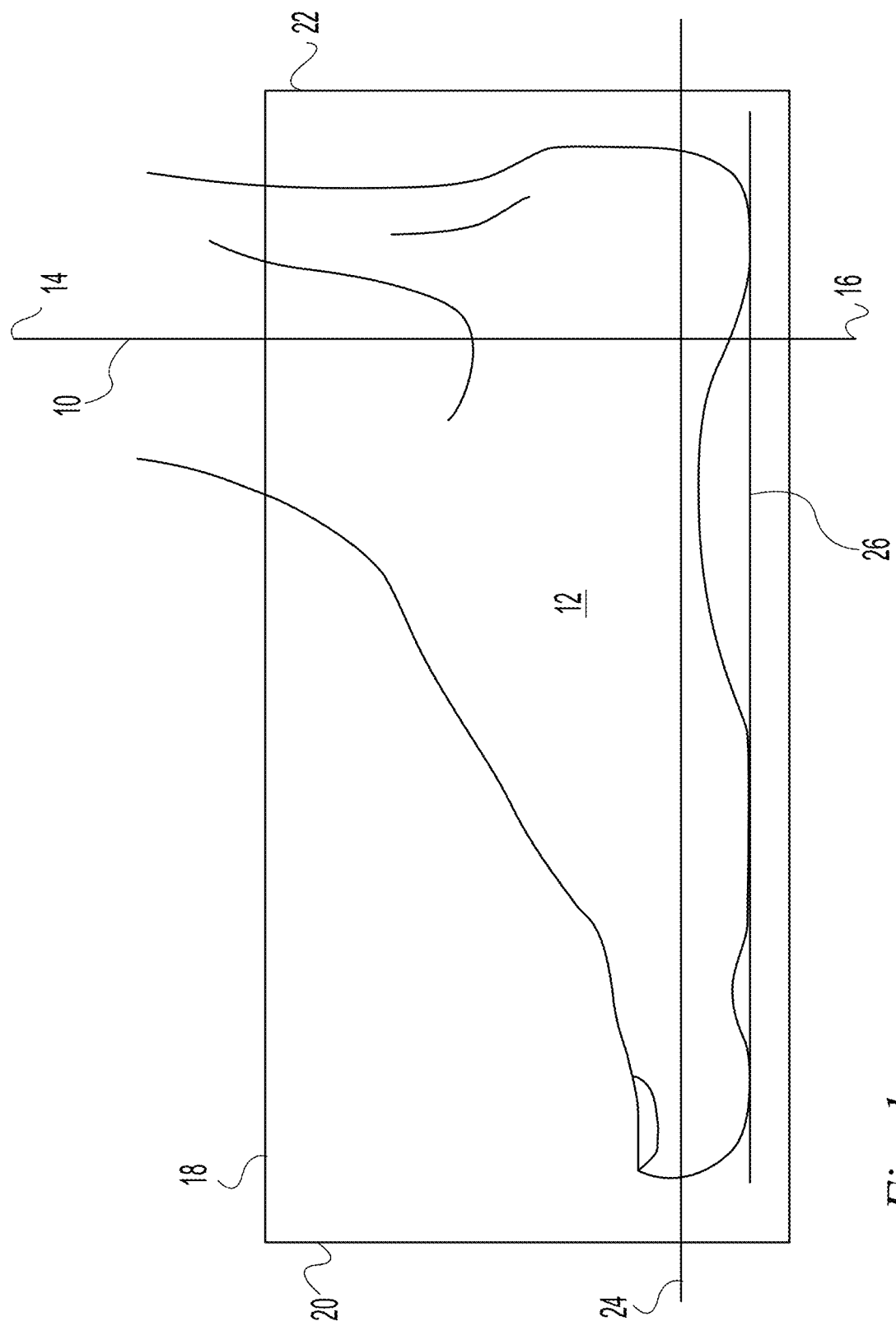
FIG. 1 is side elevation view of a foot illustrating anatomic reference planes and relative directions.

FIG. 1 illustrates the orientation of anatomic planes and relative directional terms that are used for reference in this application. The coronal plane 10 extends from medial 12 (toward the midline of the body) to lateral (away from the midline of the body) and from dorsal 14 (toward the top of the foot) to plantar 16 (toward the sole of the foot). The sagittal plane 18 extends from anterior 20 (toward the front of the body) to posterior 22 (toward the back of the body) and from dorsal 14 to plantar 16. The transverse plane 24 extends anterior 20 to posterior 22 and medial to lateral parallel to the floor 26. Relative positions are also described as being proximal or distal where proximal is along the lower extremity toward the knee and distal is along the lower extremity toward the toes. The following examples serve to demonstrate the relative directions. The great toe is medial of the lesser toes and the fifth toe is lateral of the great toe. The toes are distal to the heel and the ankle is proximal to the toes. The instep is dorsal and the arch is plantar. The toenails are dorsal and distal on the toes.

Figure 2:
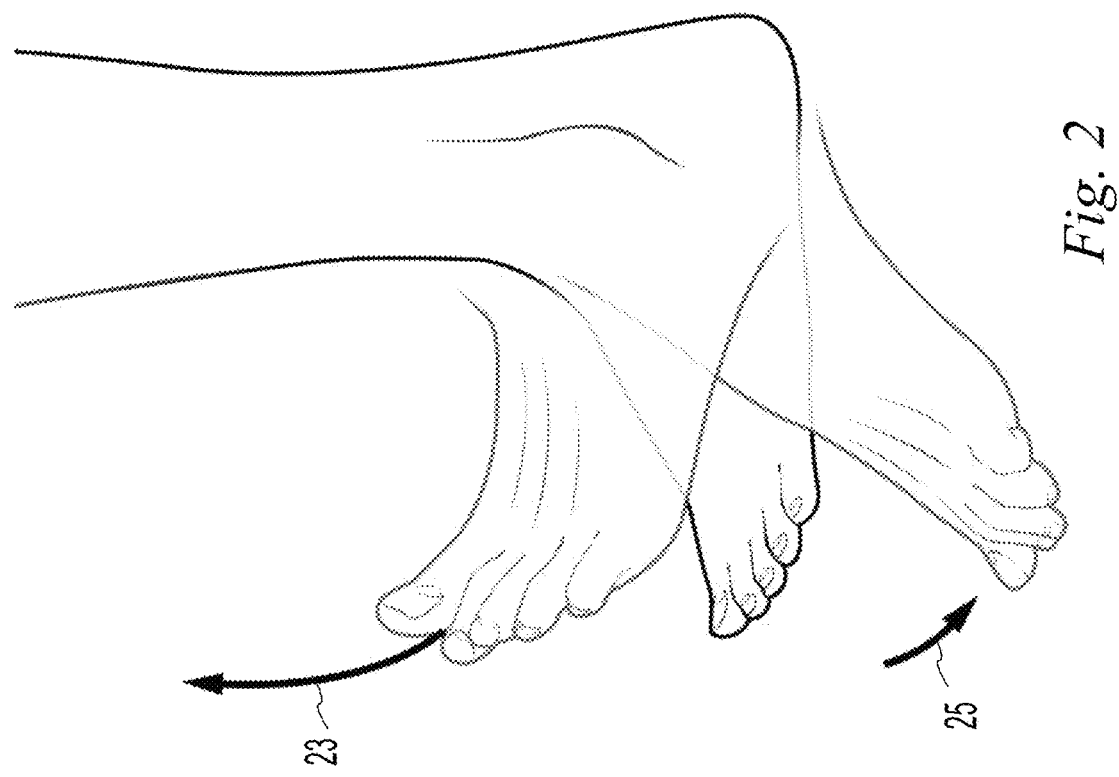
FIG. 2 is a lateral view of a foot illustrating dorsiflexion and plantar flexion.

FIG. 2 illustrates dorsiflexion 23 in which the toes are moved dorsally, or closer to the shin, by decreasing the angle between the dorsum of the foot and the leg and plantar flexion 25 in which the toes are moved plantar, or further away from the shin, by increasing the angle between the dorsum of the foot and the leg. For example when one walks on their heels, the ankle is dorsiflexed and when one walks on their toes, the ankle is plantar flexed.

Figure 3:
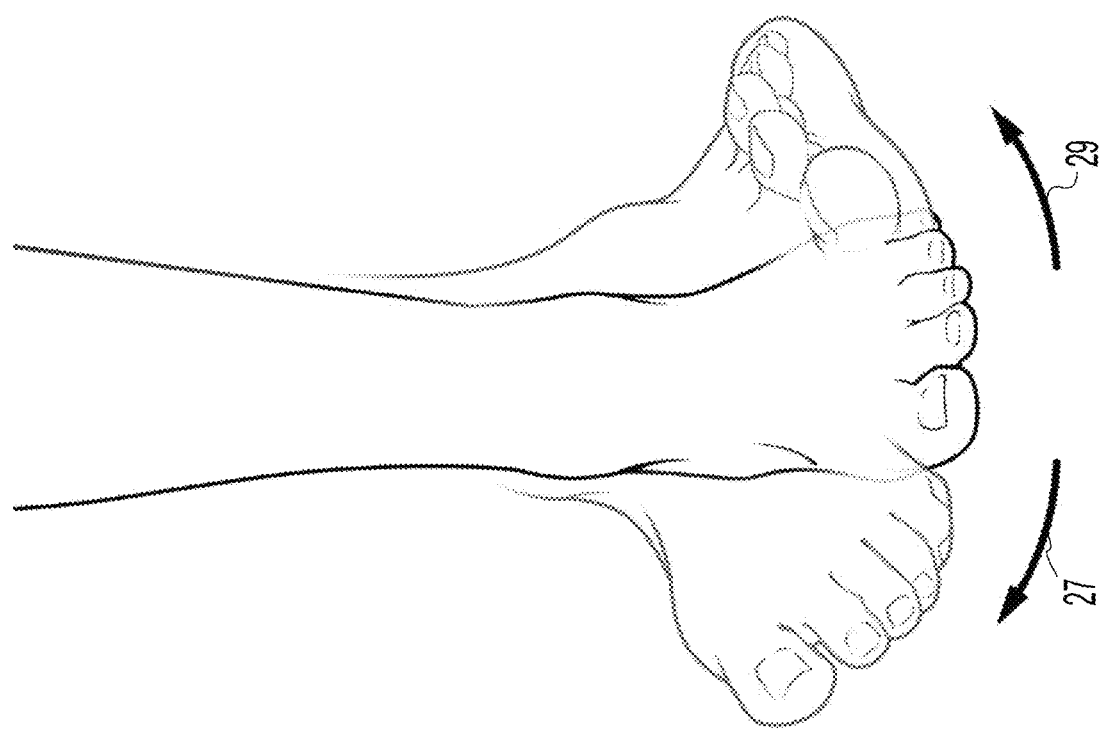
FIG. 3 is a coronal view of a foot illustrating inversion and eversion.

FIG. 3 illustrates inversion 27 in which the sole of the foot is tilted toward the sagittal plane or midline of the body and eversion 29 in which the sole of the foot is tilted away from the sagittal plane.

FIGS. 4-10 illustrate the arrangement of the bones within the foot 30. A right foot is illustrated. Beginning at the proximal aspect of the foot, the heel bone or calcaneus 32 projects plantar. The talus 34 is dorsal to the calcaneus 32 and articulates with it at the talocalcaneal or subtalar joint. Dorsally, the talus articulates medially with the tibia 36 and laterally with the fibula 38 at the ankle joint. Distal to the ankle are the navicular bone 40 medially and the cuboid bone 42 laterally which articulate with the talus and calcaneus respectively. The navicular bone 40 and cuboid bone 42 may also articulate with one another at the lateral side of the navicular bone and the medial side of the cuboid bone. Three cuneiform bones lie distal to the navicular bone and articulate with the navicular bone and one another. The first, or medial, cuneiform 44 is located on the medial side of the foot 30. The second, or intermediate, cuneiform 46 is located lateral of the first cuneiform 44. The third, or lateral, cuneiform 48 is located lateral of the second cuneiform 46. The third cuneiform 48 also articulates with the cuboid bone 42. Five metatarsals 50, 52, 54, 56, 58 extend distally from and articulate with the cuneiform and cuboid bones. The metatarsals are numbered from 1 to 5 starting with the first metatarsal 50 on the medial side of the foot and ending with the fifth metatarsal 58 on the lateral side of the foot 30. The first metatarsal 50 articulates with the first cuneiform 44 at a metatarsocuneiform (MTC) joint 51. The second metatarsal 52 articulates with the first, second and third cuneiforms 44, 46, 48 and may articulate with the first metatarsal as well. Five proximal phalanges 60, 62, 64, 66, 68 extend distally from and articulate with the five metatarsals respectively. The first proximal phalanx 60 articulates with the first metatarsal 50 at a metatarsophalangeal (MTP) joint 61. One or more distal phalanges 70, 72, 74, 76, 78 extend distally from the proximal phalanges. The first metatarsal 50, first proximal phalanx 60, and, first distal phalanx 70 together are referred to as the first ray of the foot. Similarly, the metatarsal, proximal phalanx, and distal phalanges corresponding to the lesser digits are referred to as the second through fifth rays respectively.

Figure 5:
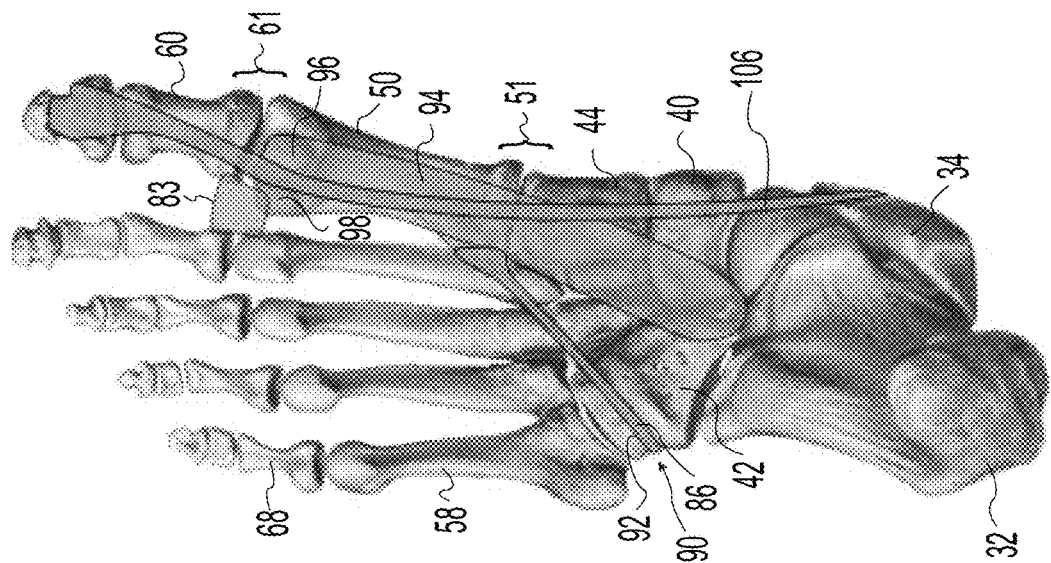
FIG. 5 is a plantar view illustrating bones, tendons, and ligaments of the foot.
Figure 4:
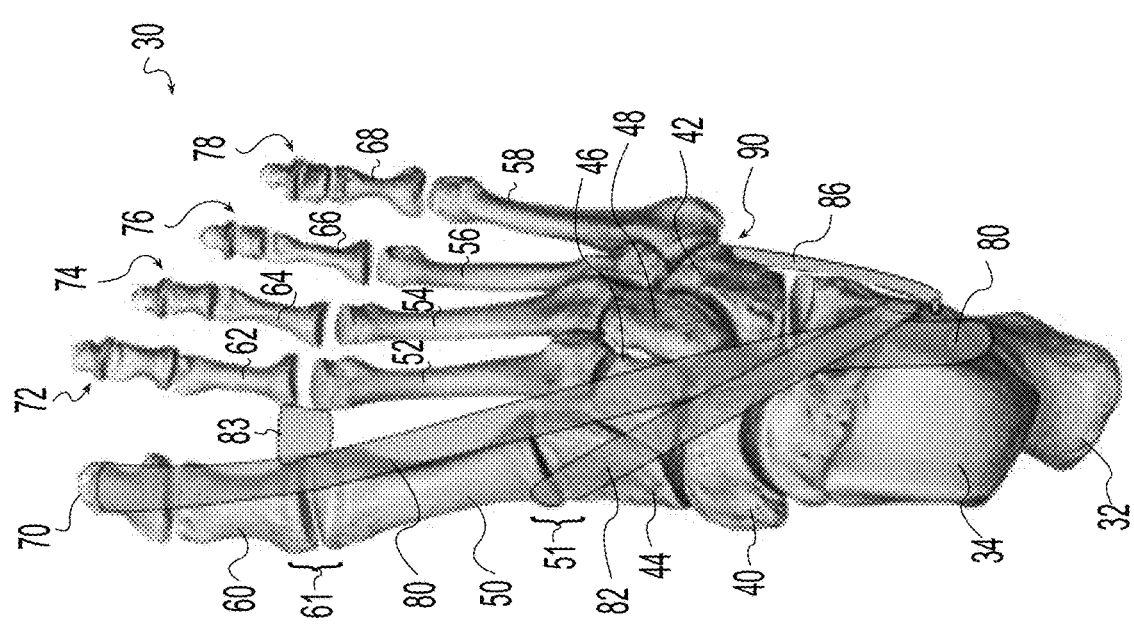
FIG. 4 is a dorsal view illustrating bones, tendons, and ligaments of the foot.
Figure 6:
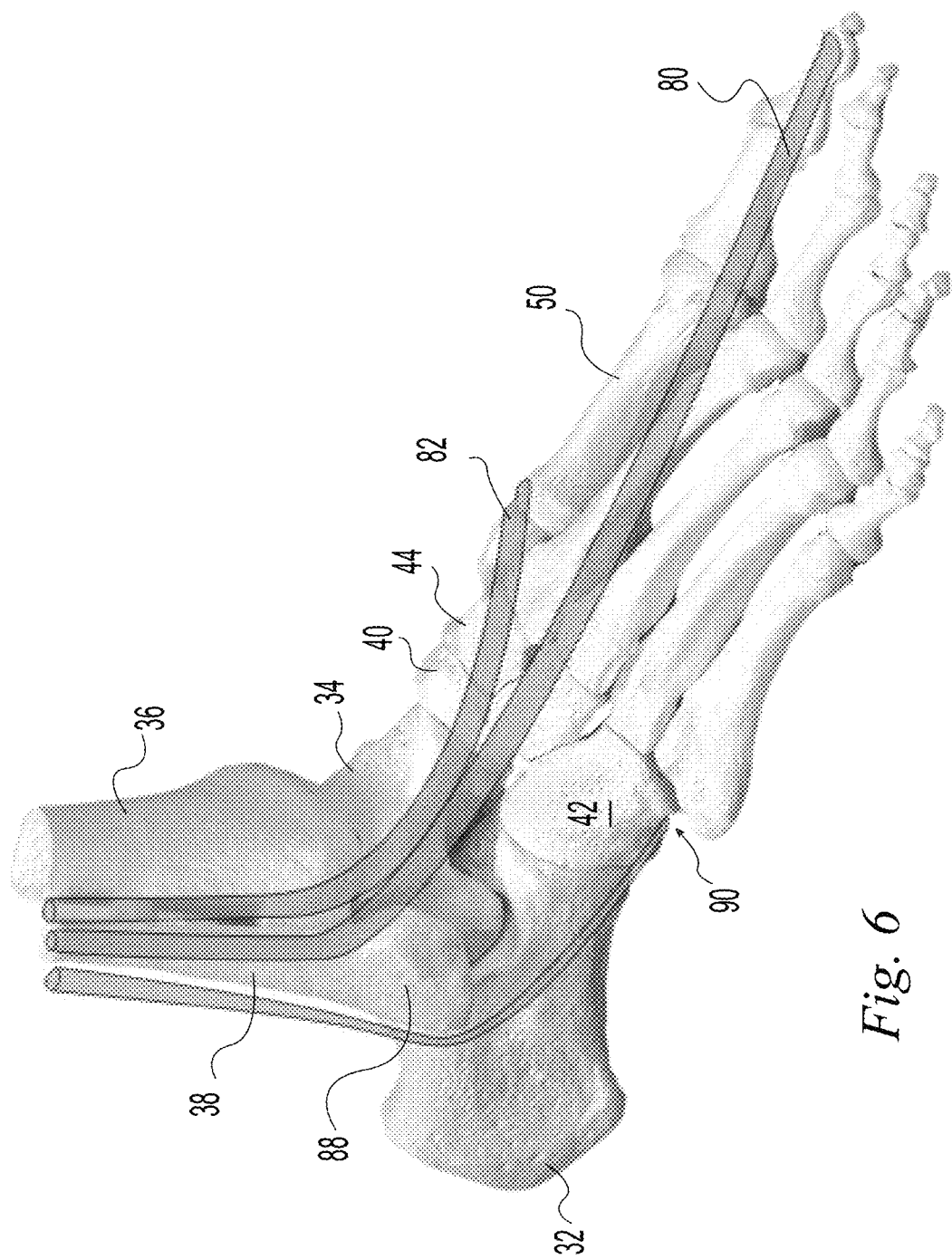
FIG. 6 is a perspective view illustrating bones, tendons, and ligaments of the foot.
Figure 10:
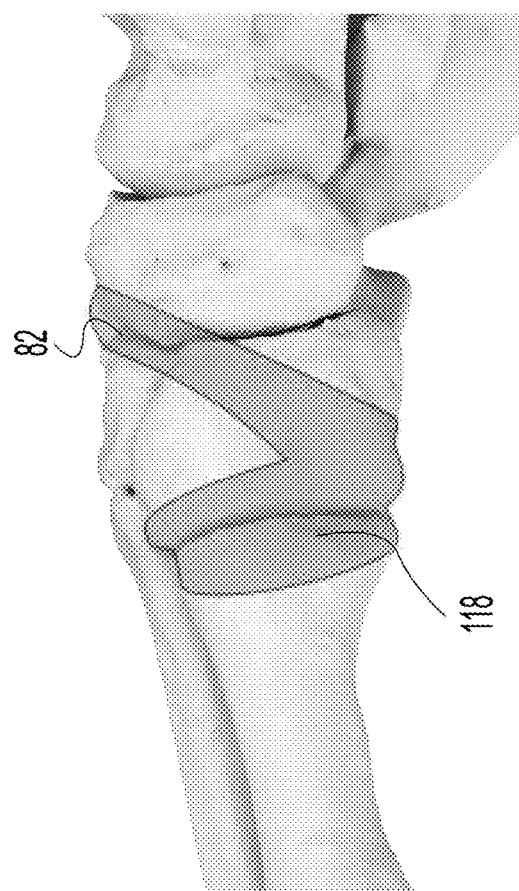
FIG. 10 is a medial view of the MTC joint of the first ray of the foot.
Figure 9:
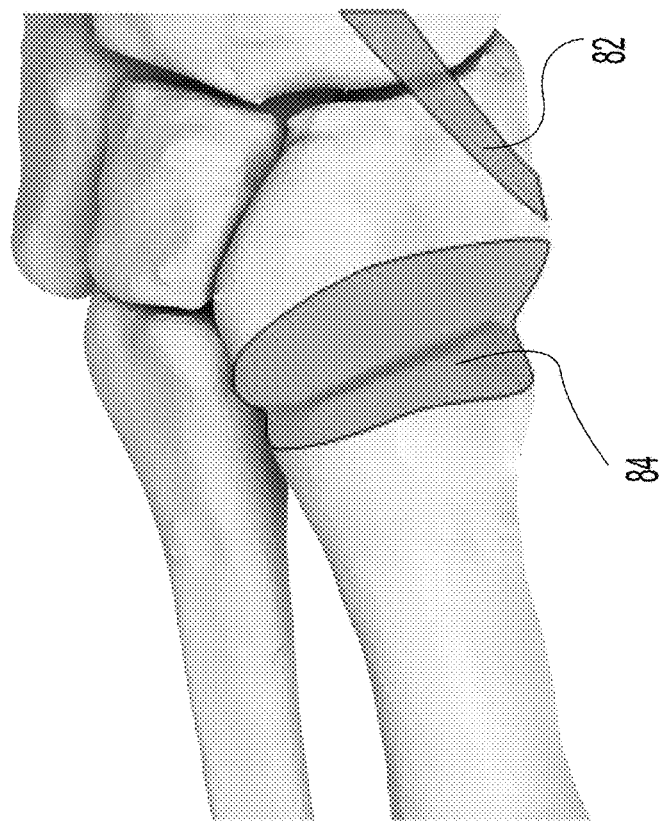
FIG. 9 is a dorsal view of the MTC joint of the first ray of the foot.

FIG. 4 is a dorsal view illustrating bones, tendons and ligaments of the foot. Plantar structures illustrated in FIG. 5 are omitted from FIG. 4 for clarity. The extensor hallucis longus muscle originates in the anterior portion of the leg, the extensor hallucis longus tendon 80 extends distally across the ankle and along the first ray to insert into the base of the distal phalanx 70. The tibialis anterior muscle originates in the lateral portion of the leg and the tibialis anterior tendon 82 extends distally across the ankle and inserts into the first cuneiform 44 and first metatarsus 50 at the first MTC joint 51 where it contributes to the MTC capsular structure 84 (FIGS. 9 and 10). A transverse intermetatarsal ligament 83 connects the heads of the first through fifth metatarsal bones. In FIG. 4, only the connection between the first and second metatarsal bones 50, 52 is shown. The intermetatarsal ligament 83 inserts into the capsule of the MTP joint.

Figure 8:
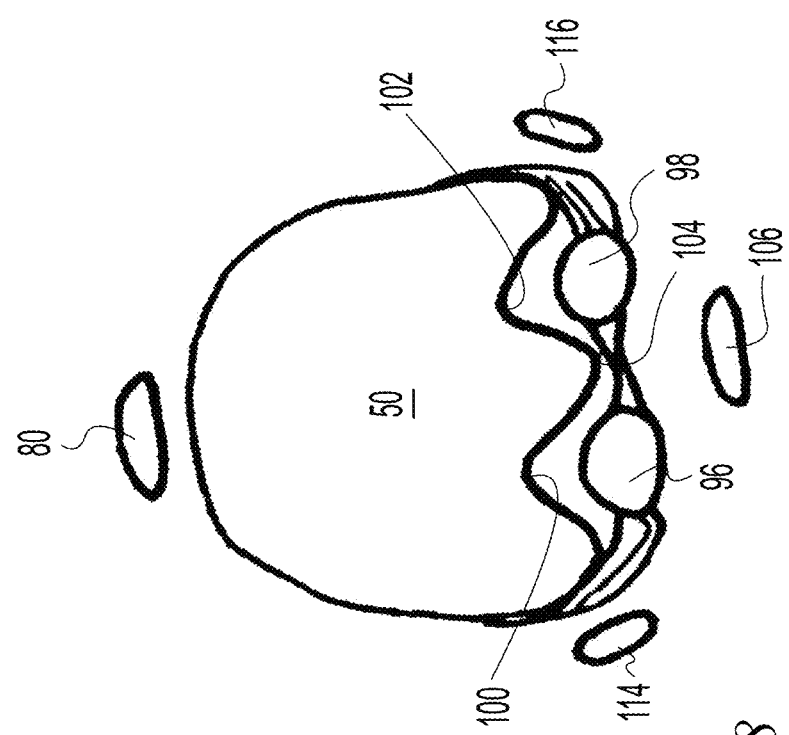
FIG. 8 is a sectional view taken along line 8-8 of FIG. 7.

FIG. 5 is a plantar view illustrating bones, tendons, and ligaments of the foot. Dorsal structures shown in FIG. 4 are omitted from FIG. 5 for clarity. The peroneus longus muscle originates at the head of the fibula and its tendon 86 passes posteriorly around the lateral malleolus 88 (FIG. 6) of the ankle, around the cuboid notch 90 on the lateral side of the cuboid bone 42, along the peroneal sulcus 92 on the plantar surface of the cuboid bone 42, and inserts into the first metatarsal 50. The flexor hallucis brevis muscle 94 originates from the cuboid 42 and third cuneiform 48 and divides distally where it inserts into the base of the proximal phalanx 60. Medial and lateral sesamoid bones 96, 98 are present in each portion of the divided tendon at the MTP joint 61. The sesamoids 96, 98 articulate with the planar surface of the metatarsal head in two grooves 100, 102 separated by a rounded ridge, or crista 104 (FIG. 8). The flexor hallucis longus muscle originates from the posterior portion of the fibula 38. The flexor hallucis longus tendon 106 crosses the posterior surface of the lower end of the tibia, the posterior surface of the talus, runs forward between the two heads of the flexor hallucis brevis 94, and is inserted into the base of the distal phalanx 70 of the great toe.

Figure 7:
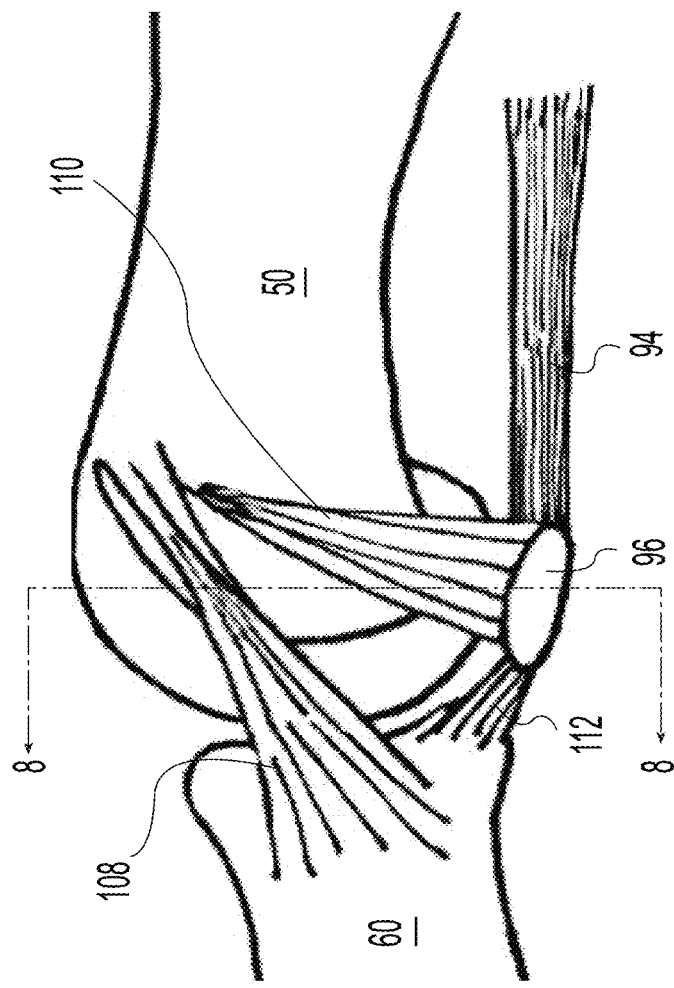
FIG. 7 is a medial view of the MTP joint of the first ray of the foot.

FIG. 7 is a medial view of tendons at the MTP joint 61 of the first ray. A medial collateral ligament 108 originates from the head of the first metatarsus 50 and inserts into the proximal phalanx 60. A medial metatarsosesamoid ligament 110 originates from the head of the first metatarsus 50 and inserts into the medial sesamoid bone 96. Similar collateral and metatarsosesamoid ligaments are found on the lateral side of the first MTP joint. The flexor hallucis brevis 94 is shown inserting into the sesamoids 96, 98. Ligamentous fibers extend further distally in the form of a phalangealsesamoid ligament 112 from the sesamoids to the proximal phalanx 60.

FIG. 8 is a sectional view taken along line 8-8 of FIG. 7 showing the metatarsal head 50, the tendon of the extensor hallucis longus 80, the medial and lateral sesamoid bones 96, 98, the grooves 100, 102 in which the sesamoids articulate, the crista 104 separating the grooves, the flexor hallucis longus 106, the abductor hallucis 114, and the adductor hallucis 116.

FIG. 9 is a dorsal view showing the dorsal capsular structure 84 of the MTC joint 51 of the first ray including the insertion of the tibialis anterior tendon 82.

FIG. 10 is a medial view of the MTC joint 51 of the first ray showing the medial capsular structure 118.

Figure 12:
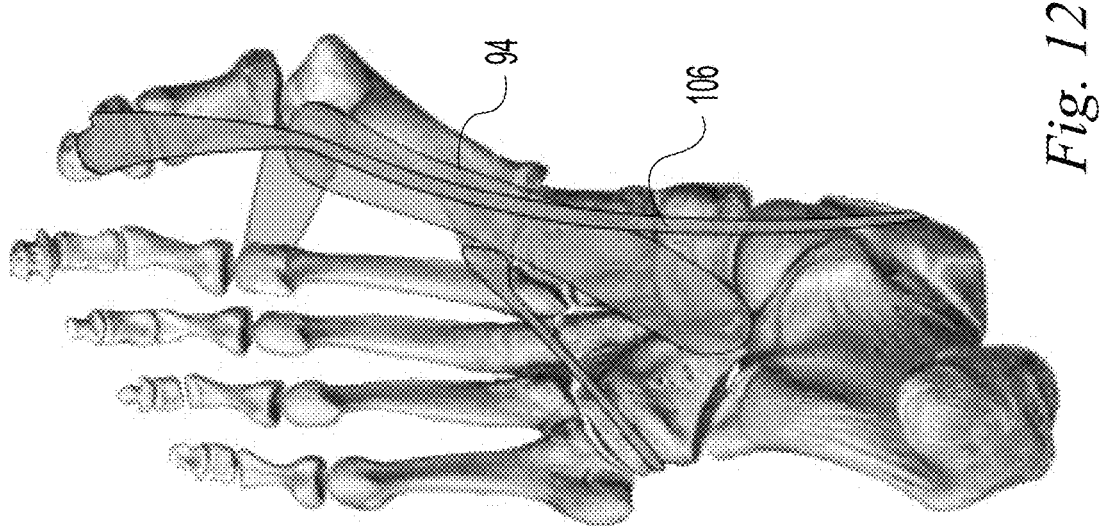
FIG. 12 is a plantar view illustrating deformity of the foot.
Figure 11:
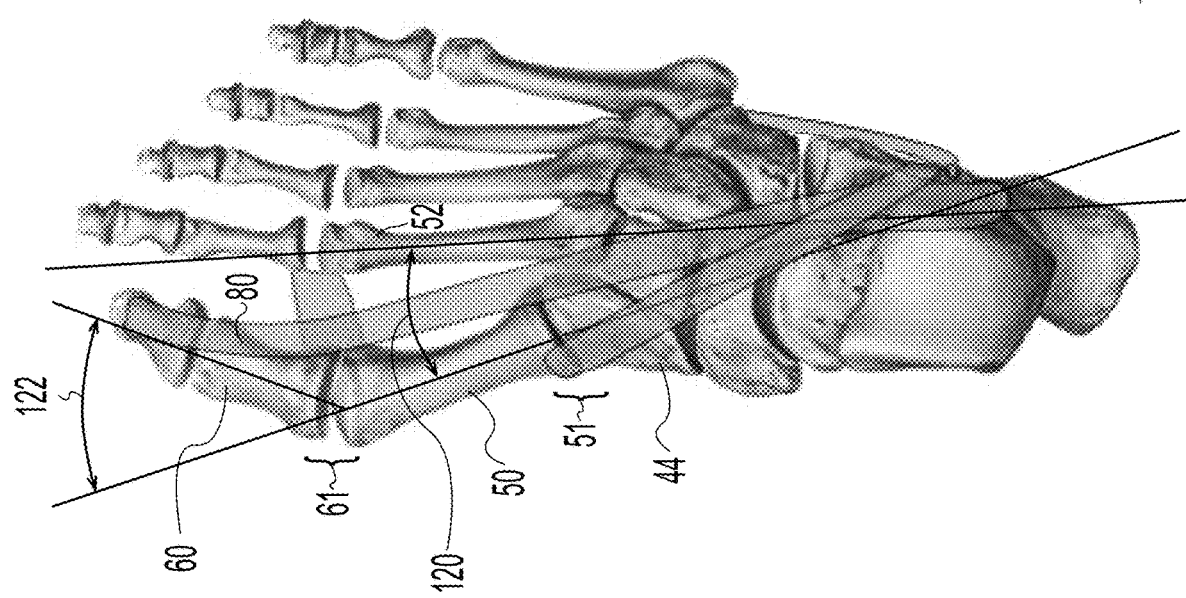
FIG. 11 is a dorsal view illustrating deformity of the foot.
Figure 13:
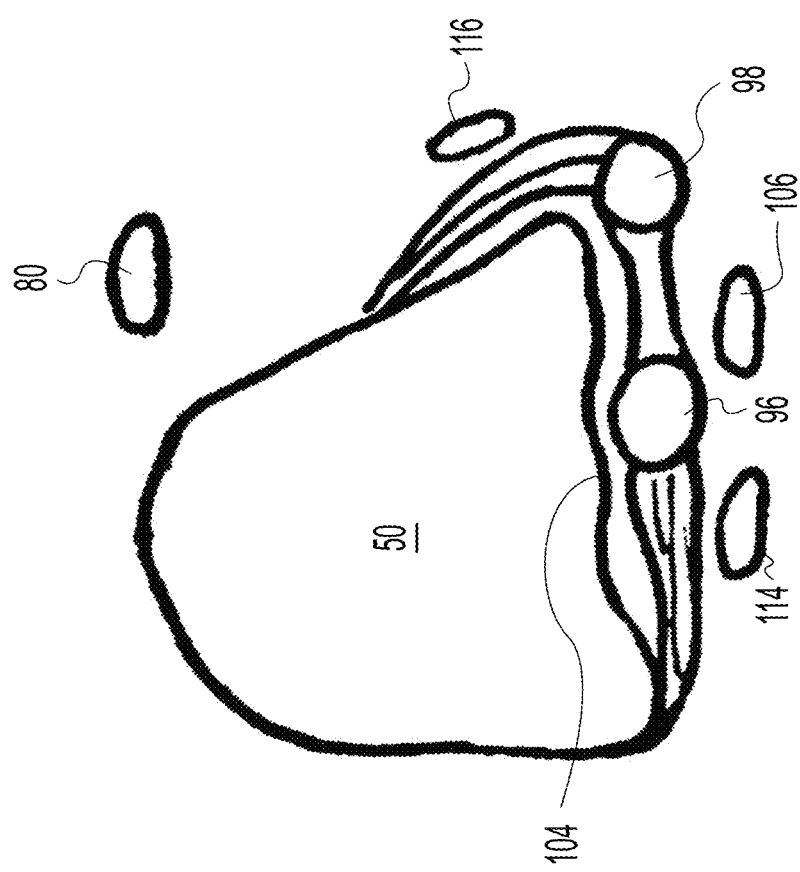
FIG. 13 is a sectional view similar to that of FIG. 8 but illustrating deformity of the foot.
Figure 14:
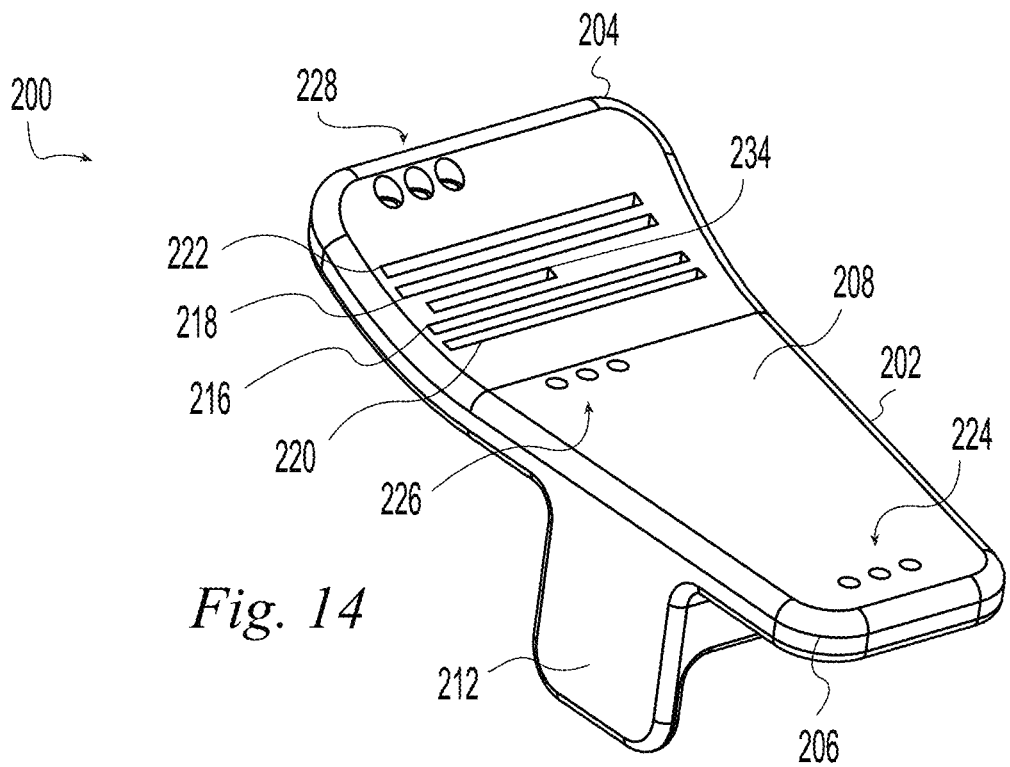
FIG. 14 is a perspective view of an osteotomy guide according to the present invention.
Figure 15:
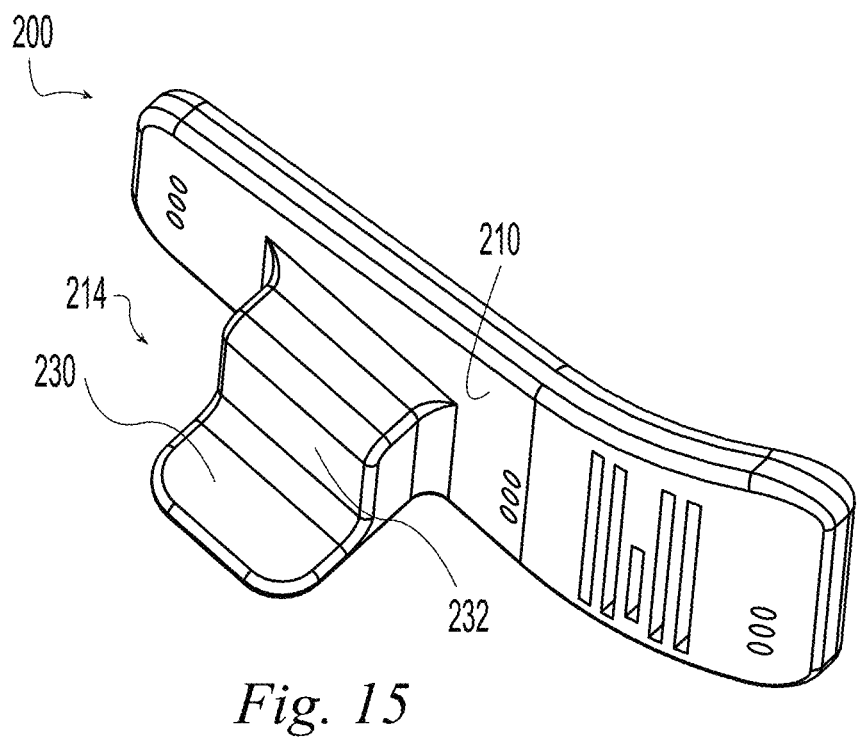
FIG. 15 is a another perspective view of the osteotomy guide of FIG. 14.
Figure 16:
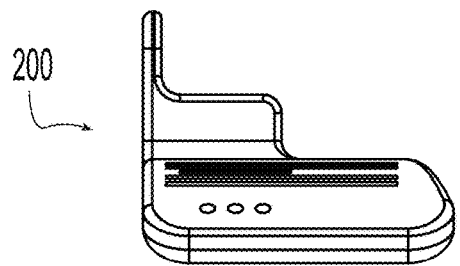
FIG. 16 is a front elevation view of the osteotomy guide of FIG. 14.

FIGS. 11-13 illustrate deformities of the first ray. In a dorsal view, as shown in FIG. 11, an intermetatarsal angle (IMA) 120 may be measured between the longitudinal axes of the first and second metatarsal bones 50, 52. The angle is considered abnormal when it is 9 degrees or greater and the condition is known as metatarsus primus varus (MPV) deformity. A mild deformity is less than 12 degrees, a moderate deformity is 12-15 degrees, and a severe deformity is greater than 15 degrees. Similarly, a hallux valgus angle (HVA) 122 may be measured between the longitudinal axes of the first metatarsus 50 and the first proximal phalanx 60 at the MTP joint 61. The angle is considered abnormal when it is 15 degrees or greater and the condition is known as a hallux valgus (HV) deformity. A mild deformity is less than 20 degrees, a moderate deformity is 20 to 40 degrees, and a severe deformity is greater than 40 degrees.

MPV and HV often occur together as shown in FIGS. 11-12. As the deformities progress several changes may occur in and around the MTC and MTP joints. Referring to FIG. 13, as the IMA and HVA increase, the extensors 80, flexors 106, abductors 114, and adductors 116 of the first ray (along with the sesamoids 96, 98) are shifted laterally relative to the MTP joint. The laterally shifted tendons exert tension lateral to the MTP joint creating a bow string effect (as best seen in FIGS. 11 and 12) that tends to cause the deformities to increase. The lateral shift of the sesamoids 96, 98 is often accompanied by erosion of the crista. The abnormal muscle forces cause the metatarsus 50 to pronate, or in other words, rotate so that the dorsal aspect of the bone moves medially and the plantar aspect moves laterally. Rotation in the opposite direction is referred to as supination. Soft tissues on the medial side of the MTP joint and lateral side of the MTC joint attenuate, through lengthening and thinning, thus weakening the capsule and permitting the deformities to progress. Soft tissues on the opposite sides of the capsule tend to shorten, thicken and form contractures making it difficult to reduce the joints to their normal angular alignment.

More generally, deformities of the first ray may include metatarsus primus varus, hallux valgus, abnormal pronation, abnormal supination, abnormal dorsiflexion, and/or abnormal plantar flexion. These deformities correspond to three different planar rotations. Metatarsus primus varus and hallux valgus result from rotations in the transverse plane 24. Pronation and supination are rotation in the coronal plane 10. Dorsiflexion and plantar flexion are rotation in the sagittal plane.

The terms "suture" and "suture strand" are used herein to mean any strand or flexible member, natural or synthetic, able to be passed through material and useful in a surgical procedure. The term "transverse" is used herein to mean crossing as in non-parallel.

The present invention provides methods and devices for performing an osteotomy. FIGS. 14-20 depict an illustrative osteotomy guide 200 according to the present invention. The guide 200 includes a guide body 202 having a proximal end 204, a distal end 206, a first side 208, a second side 210 opposite the first side 208, an upper surface 212, and a lower surface 214.

The guide body 202 includes first and second guide features operable to guide a cutter to cut a bone. In the illustrative example of FIGS. 14-20, the guide features include a first slot 216 and a second slot 218 for receiving a cutter, such as a saw blade, to constrain the cutter to cutting in a plane. In the illustrative example of FIGS. 14-20, the slots 216, 218 are narrow and constrain a saw blade from both sides. Alternatively, a guide feature configured for a saw blade may include a single surface against which the saw blade is pressed to guide it in a plane. Additional guide features, such as slots 220, 222, may be provided to, e.g., provide alternative spacing of cuts or the option to recut if additional bone removal is desired. The guide features may guide a cutter in parallel planes or they may be angled relative to one another to produce cuts in non-parallel planes. In the illustrative example of FIGS. 14-20, the slots 216, 218, 220, 222 are parallel.

The guide body 202 includes fixation elements for attaching the guide 200 to underlying bone. Fixation elements may include spikes, slots, holes, bands or other suitable fixation elements. The fixation elements may act alone, as with a spike or band, or they may work with additional fixation members such as pins or screws. In the illustrative example of FIGS. 14-20, the guide body 202 includes fixation elements in the form of holes operable to receive pins or screws to attach the guide 200 to bone. In the illustrative example of FIGS. 14-20, two sets of holes 224, 226 are provided distal to the guide slots 216, 218, 220, 222 and another set 228 is provide proximal to the guide slots. The distal sets of holes 224, 226 may, e.g., may be used to attach the guide to a first bone portion prior to a first bone cut and the proximal set of holes 228, e.g., may be used to attach the guide to a second bone portion prior to a second bone cut as will be described in further detail below.

In the illustrative example of FIGS. 14-20, the guide body includes first and second indexing features engageable with a bone to align the guide relative to the bone. For example, a first indexing feature 230 in the form of a planar surface and a second indexing feature 232 in the form of a planar surface may be angled relative to one another so that the first and second indexing features may engage different sides of a bone to provide bi-planar orientation of the guide relative to a bone.

The guide 200 may be used to cut portions of the same bone or portions of different bones where they meet at a joint. The guide body 202 may include a joint alignment feature to aid in positioning the guide body 202 relative to a joint. The joint alignment feature allows a user to position the guide relative to a joint. For example, the joint alignment feature may be an opening for visualizing the alignment, a projection from the guide body 202 engageable with the joint, an opening for receiving a member engageable with the joint, or other suitable joint alignment feature. In the illustrative example of FIGS. 14-20, the guide body includes a joint alignment feature in the form of a slot 234 able to receive a feeler gauge, or shim, for positioning the joint alignment feature over the joint. The joint alignment slot 234 is positioned in a predetermined relationship to the guide slots 216, 218, 220, 222 so that a cutter guided by the guide slots will remove a predetermined amount of bone from the bones forming the joint.

Figure 17:
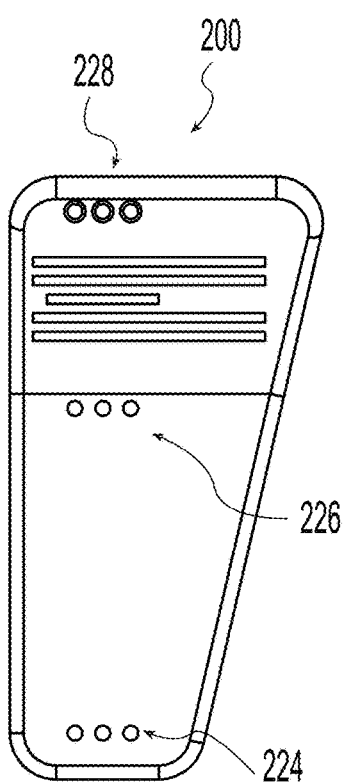
FIG. 17 is a side elevation view of the osteotomy guide of FIG. 14.
Figure 18:
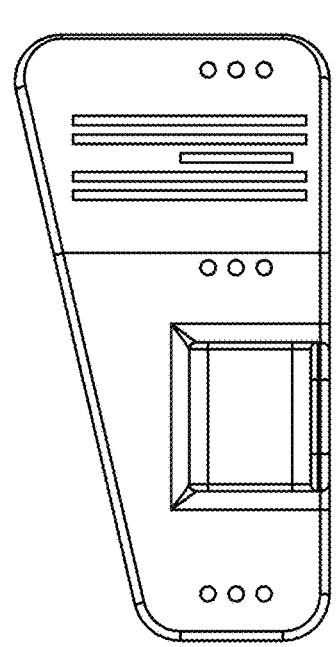
FIG. 18 is a top plan view of the osteotomy guide of FIG. 14.
Figure 19:
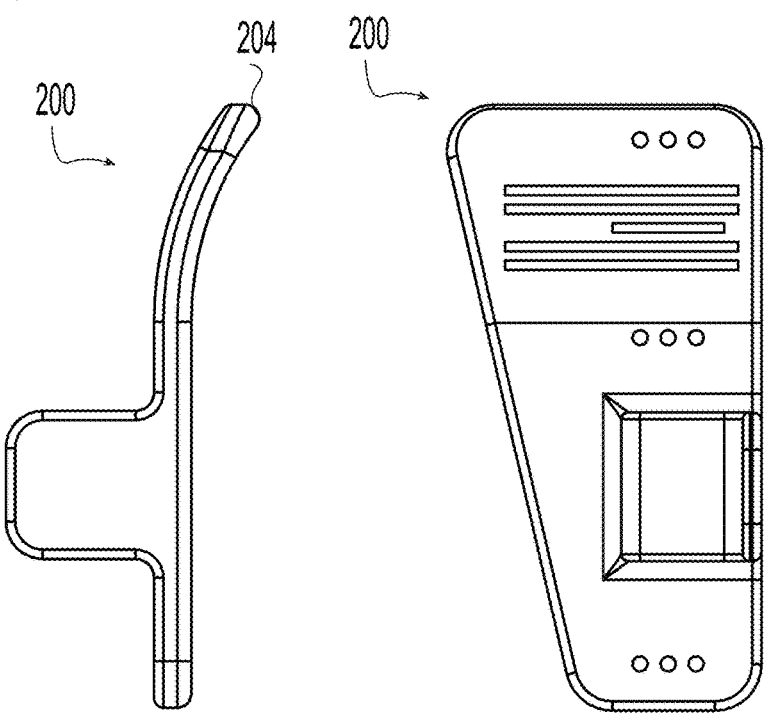
FIG. 19 is a side elevation view of the osteotomy guide of FIG. 14.
Figure 20:
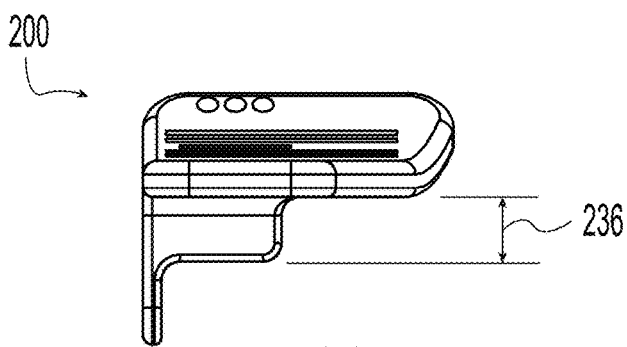
FIG. 20 is a rear elevation view of the osteotomy guide of FIG. 14.

The guide 200 may be configured for use on any single bone or on any bones forming a joint. The particular shape and size of the guide and its various features as described above may be varied to suit the particular bone or joint. For example, the illustrative guide of FIGS. 14-20, is configured for use at the metatarsocuneiform joint of the first ray of a right human foot. The guide body 202 has a generally trapezoidal shape when viewed from the side (FIGS. 17 and 19). The distal sets of holes 224, 226 are positioned to allow at least one pin to be inserted through each set of holes and into the medial side of a first metatarsus. The proximal end 204 flairs outwardly to clear the medial cuneiform. The proximal set of holes 228 is positioned to allow pins to be inserted through them and into the medial cuneiform. The first and second indexing features 230, 232 are sized to engage the diaphysis of the metatarsus to align the guide 200 generally parallel to the metatarsal axis. The first and second indexing features 230, 232 are offset a distance 236 (FIG. 20) from the second side 210 of the guide body 202 to space the second side 210 from the metatarsus sufficiently to provide clearance for the metaphyseal flair at the ends of the metatarsus to insure that the guide is indexed to the relatively consistent geometry of the diaphysis rather than the more variable geometry of the metaphysis. The joint alignment slot 234 and guide slots 216, 218 are positioned so that with the joint alignment slot 234 aligned with the metatarsocuneiform joint, a cutter guided by the guide slots 216, 218 will remove a predetermined, and relative thin, portion of bone from the articulating ends of the metatarsus and cuneiform. The additional guide slots 220, 222 are positioned relative to the joint alignment slot 234 to permit additional bone to be removed if desired.

An illustrative method according to the present invention produces an osteotomy between a first bone portion and a second bone. The bones define a first relative position between them. The method includes cutting the first bone portion, moving the bone portions to a second relative position different from the first relative position, and cutting the second bone portion. For example, to realign first and second bone portions to correct an angular deformity, the first bone portion may be cut to form a cut surface on the first bone portion and allow the first bone portion to be freely mobilized relative to the second bone portion. The bone portions may be positioned in a new relative orientation that reduces the angular deformity between them. The second bone portion may then be cut to form a cut surface on the second bone. The cut surfaces may be brought together to promote fusion of the bone portions in the new relative orientation. Alternatively, a graft may be positioned between the cut surfaces to prevent a change in length of the bone construct. The bone portions may be portions of the same bone in the case of an osteotomy to change the shape of a bone. The bone portions may be portions of different bones forming a joint in the case of an osteotomy to change the angular relationship between the bones and fuse the joint in the new angular relationship.

For example, in a deformity of a human foot, the relative position of the metatarsus and cuneiform at the metatarsocuneiform joint may be changed. For example, a first cut may be made on one of the metatarsus and cuneiform to remove a portion of bone creating a first cut surface and a space resulting in increased mobility between the metatarsus and cuneiform to allow them to be freely repositioned. The bones may be repositioned in one or more planes. For example, the metatarsus may be rotated laterally in the transverse plane to correct an MPV deformity, rotated in the coronal plane to correct abnormal pronation/supination, and rotated in the sagittal plane to adjust plantar/dorsal flexion. Once the new position is established, the cuneiform may be cut to create a second cut surface in predetermined relationship (as determined by the cut guide features) to the first cut surface. The first and second cut surfaces may be brought together and fixed so that they heal together fusing the joint in the new position.

To avoid shortening of the bone construct, a graft or other spacer may be placed in the gap between the bones to maintain their separation in the new position. For example, the spacer may be autograft, allograft, xenograft, synthetic graft, metal, plastic, ceramic, solid filler, particulate filler or other suitable spacer.

The bone portions may be fixed relative to one another to promote healing with fixation elements such as pins, plates, screws, rods or other suitable fixation elements.

In some cases it is advantageous for the first and second cut surfaces to be parallel planar surfaces, e.g., to facilitate abutting them together or with a solid parallel faced spacer to easily maintain the new position of the bones. In other cases, it may be desirable to angle the surfaces, e.g., to accommodate a wedge shaped spacer that may be easier to insert or to produce an additional amount of angular correction, e.g., to produce a few degrees of additional plantarflexion to account for bone shortening where a graft is not used.

A method according to the invention may be performed freehand or with the use of an osteotomy guide. The use of an osteotomy guide, such as that shown in FIGS. 14-20, results in more precision and repeatability in the relative orientation of the cuts. Being able to produce a predefined gap facilitates providing preformed spacers that will fit the gap and lock in the new position of the bones.

FIGS. 21-25, depict an illustrative method of performing an osteotomy. In the illustrative example of FIGS. 21-25, the optional osteotomy guide of FIGS. 14-20 is used to perform an osteotomy at the metatarsocuneiform joint of the first ray of a foot for fusing the joint in a new position.

Figure 21:
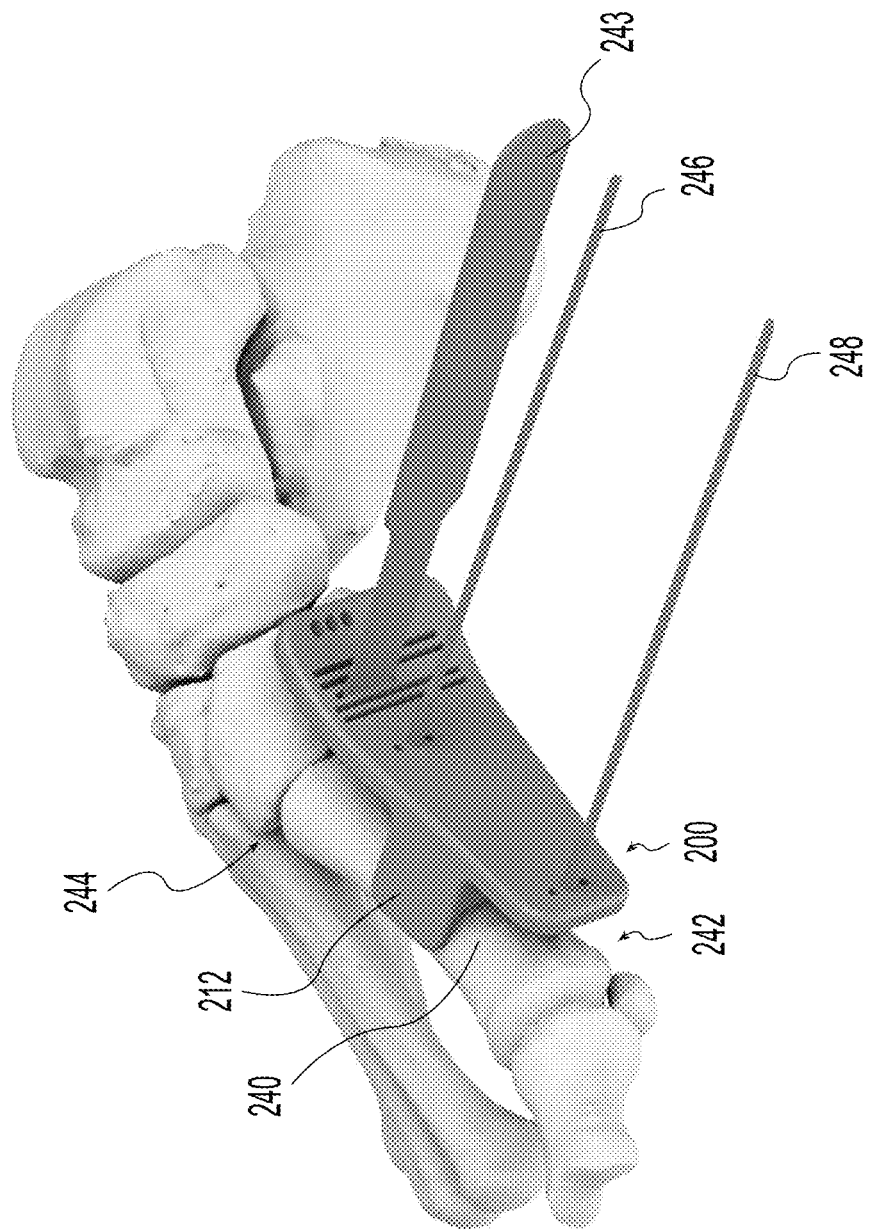
FIGS. 21-25 illustrate the use of the osteotomy guide of FIG. 14 to perform an osteotomy.

In FIG. 21, the first and second indexing features 230, 232 are abutted against the diaphysis 240 of the metatarsus 242. In the illustrative example of FIGS. 21-25, the indexing features are shown engaging the dorsal and medial aspects of the diaphysis 240. However, the guide can be positioned in other orientations around the joint. For example, the indexing features 230, 232 may be engaged with the lateral and dorsal aspects of the diaphysis 240 or some other position to facilitate surgical access. Downward and lateral pressure may be exerted on the guide such as by pressing on upper surface 212 to keep the guide 200 engaged with the bone. A feeler gauge 243, or shim, is inserted through the joint alignment slot 234 and used to align the guide 200 with the metatarsocuneiform joint 244. Pins 246, 248 are placed through the fixation holes 224, 226 to fix the guide 200 to the metatarsus 242.

Figure 22:
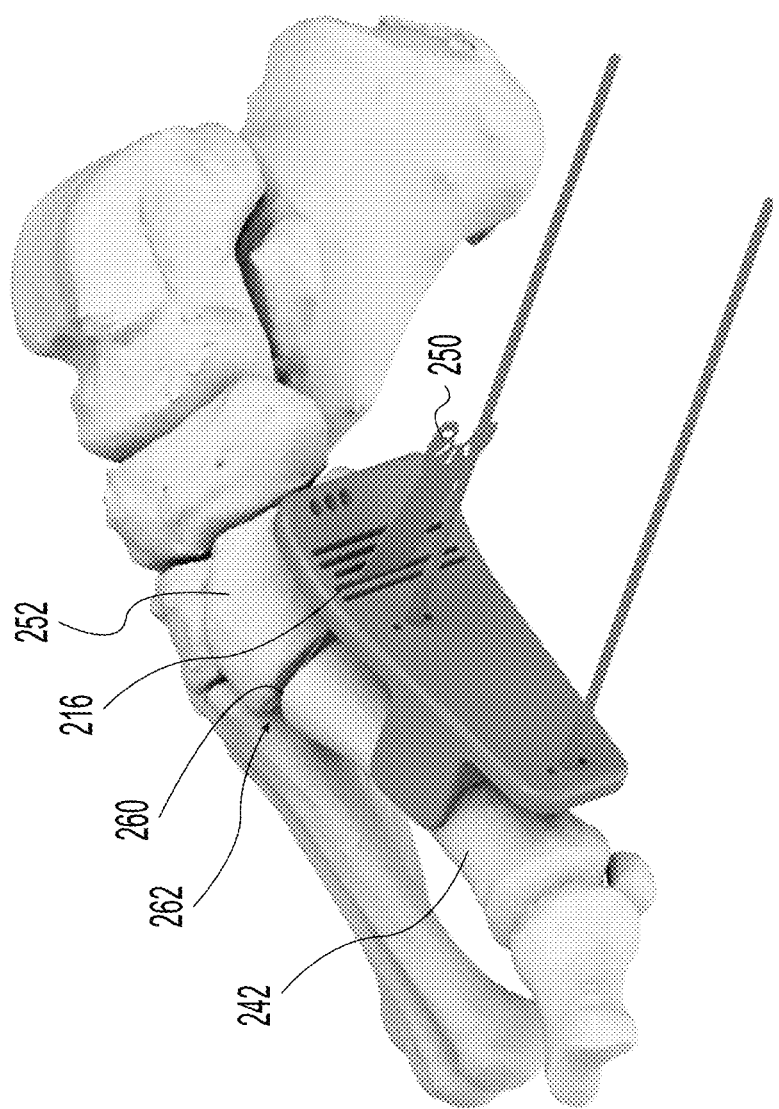

In FIG. 22, a saw blade 250 in a powered handpiece (not shown) is guided in one of the distal guide slots 216 to remove bone from the proximal end of the metatarsus 242. This creates a first planar cut surface 260 and a gap 262 and increases the mobility between the metatarsus 242 and cuneiform 252.

Figure 23:
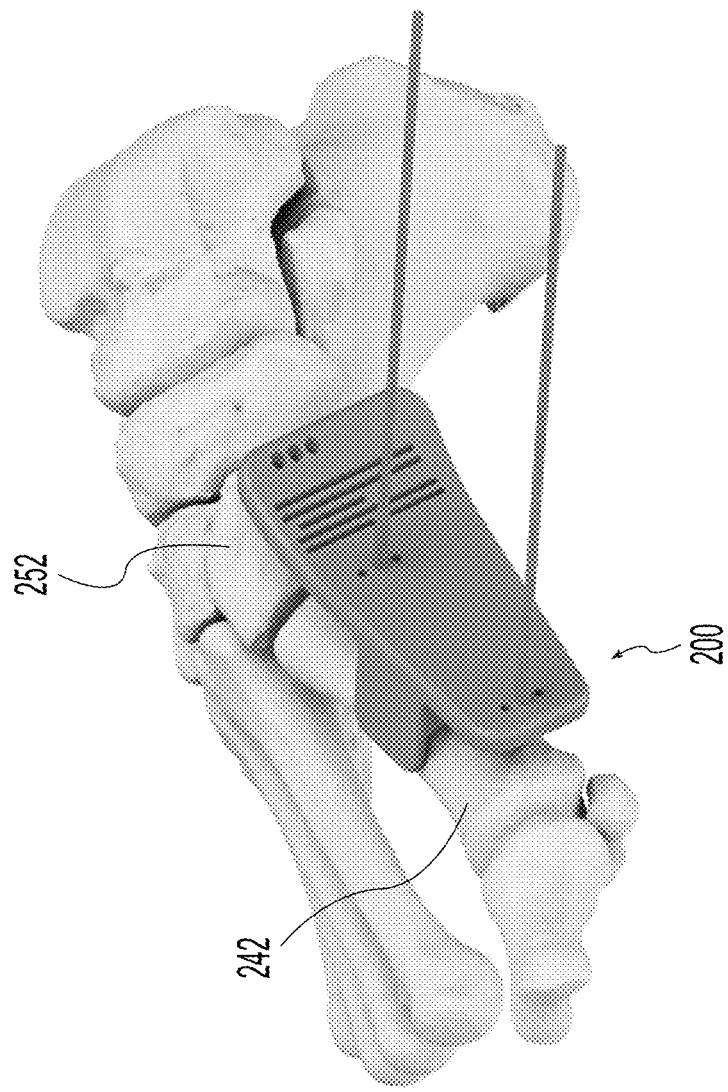

In FIG. 23, the metatarsus 242 is repositioned relative to the cuneiform 252 to change their relative position in one or more planes. Because the guide 200 is fixed to the metatarsus 242, the guide 200 moves with the metatarsus 242 and the position of the guide 200 relative to the metatarsus does not change insuring that the relationship of the guide slots 216, 218, 220, 222 to the cut surface of the metatarsus also remains unchanged.

Figure 24:
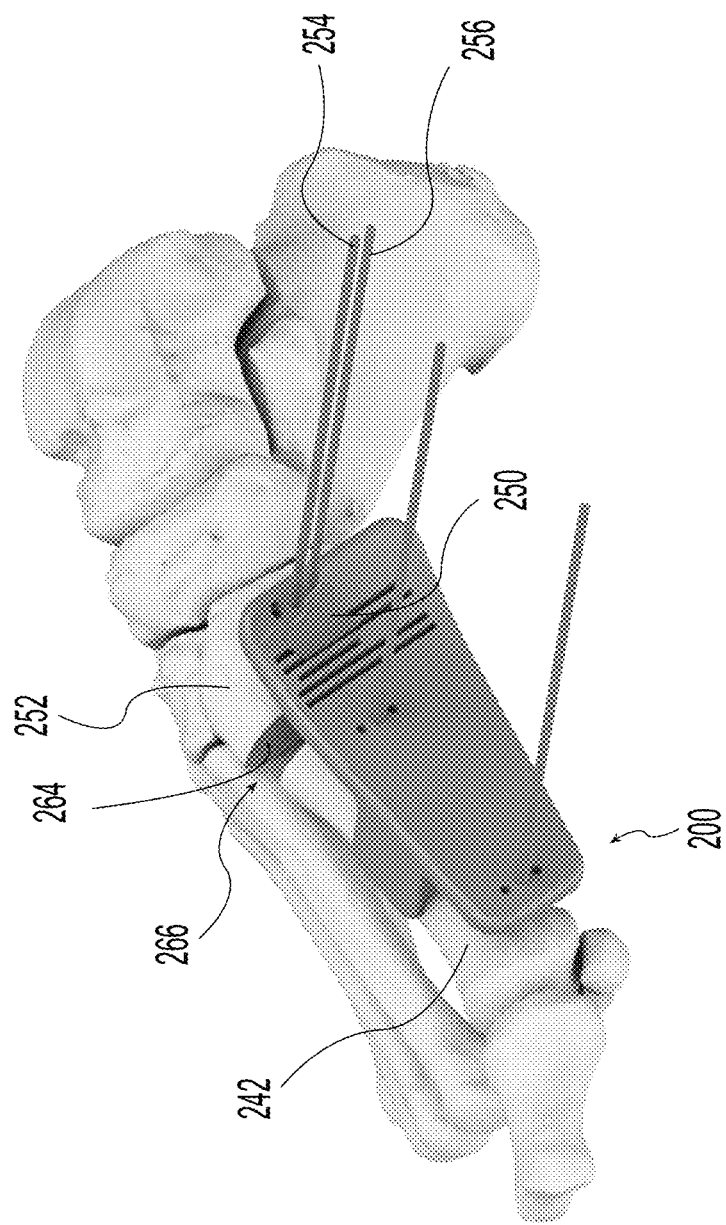
Figure 25:
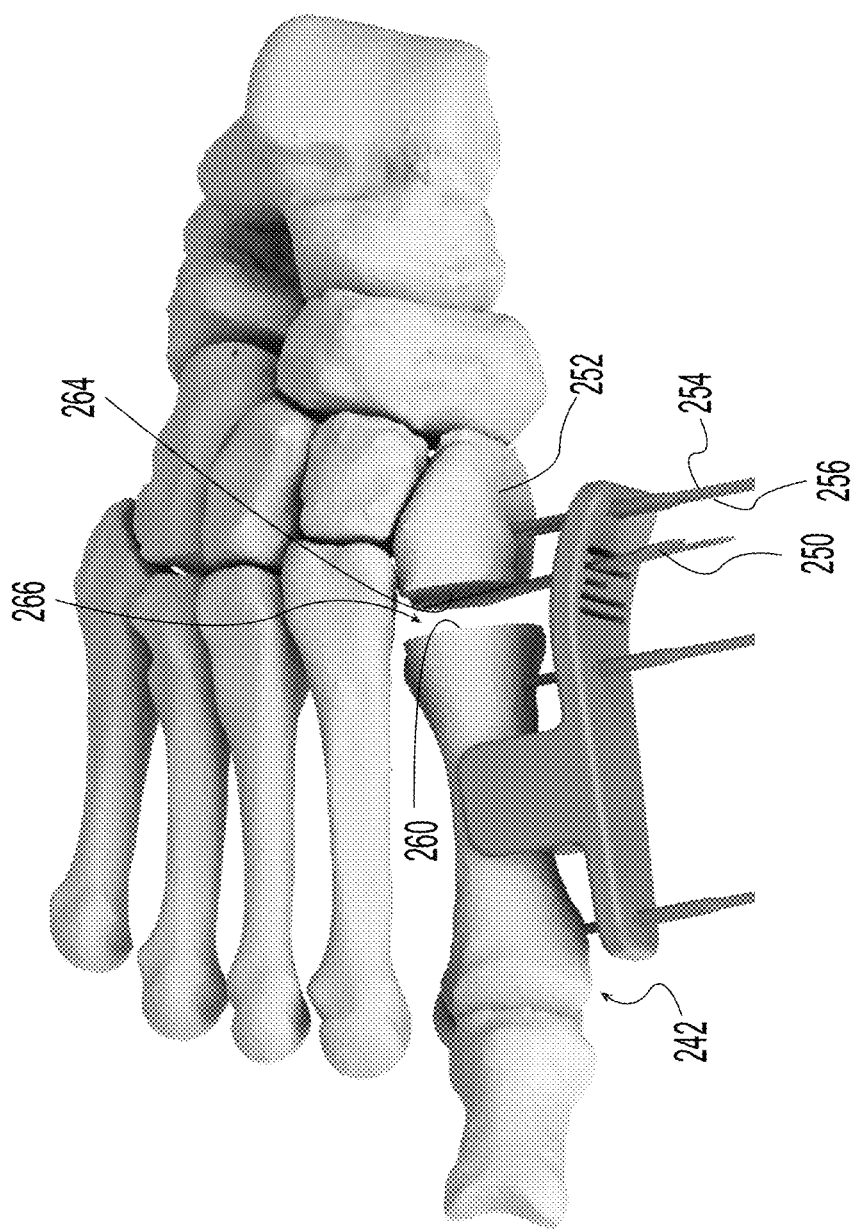

In FIGS. 24 and 25, once the bones are oriented in a desired new position, pins 254, 256 are placed in the proximal fixation holes 228 to fix the metatarsus 242, and guide 200, in the new position relative to the cuneiform 252. A saw blade 250 is guided in one of the proximal guide slots 218 to remove bone from the distal end of the cuneiform 252. This creates a second planar cut surface 264 on the cuneiform 252 in predetermined relationship to the first planar cut surface 260 on the metatarsus 242 and a gap 266 between the bones having a predetermined shape. In the illustrative example of FIGS. 21-25, the cut surfaces 260 and 264 are parallel.

The guide 200 may be removed and the bones brought together with their cut surfaces in planar contact so that the bones fuse together in the new angular orientation. Alternatively, a spacer may be placed in the gap 266 in engagement with the cut surfaces 260, 264 to maintain the bone construct length while the bones fuse together in the new angular orientation. As seen in FIG. 25, the guide 200 may be used to hold the bones in the desired orientation while a spacer is inserted and any additional fixation in the forms of pins, plates, screws, rods or other suitable fixation is applied.

FIGS. 26 and 27 depict an illustrative osteotomy guide 300 according to the present invention. The guide 300 is similar to that of FIGS. 14-20. However, the guide 300 includes a guide body 302 having a separate proximal member 304 and distal member 306 that are engaged in linear sliding relationship. In the illustrative example of FIGS. 26 and 27, the distal member 306 includes a dovetail slot 308 formed in the first side 310 and extending from the proximal end 312 of the distal member 306 toward the distal end 314. The slot 308 defines a linear motion axis 316. The proximal member 304 includes a dovetail arm 318. The slot 308 and arm 318 have complementary cross sectional shapes so that the arm fits closely within the slot and the proximal and distal members 304, 306 are constrained to linear sliding motion along the motion axis 316. The proximal member 304 is offset relative to the distal member 306 so that the proximal member may slide over the distal member. In the illustrative example of FIGS. 26 and 27, the guide 300 is shown configured for a right first metatarsus and the proximal member 304 is offset medially relative to the distal member 306.

Indicia 334, including tic marks and associated reference numbers, are formed adjacent to the slot 308. As the arm 318 slides within the slot 308, the end 336 of the arm may be aligned with the indicia to indicate the relative position of the proximal and distal members 304, 306. For example, in the illustrative example of FIGS. 26 and 27, the indicia indicate the spacing, in millimeters, between the saw slots 324, 330. A locking mechanism is provided to lock out motion between the proximal and distal members 304, 306. In the illustrative example of FIGS. 26 and 27, the locking mechanism is a locking screw 340 threaded through the arm and engageable with the wall of the slot. Tightening the screw 340 into contact with the slot wall locks the mechanism and loosening the screw 340 out of contact with the slot wall unlocks the mechanism.

The distal member 306 includes proximal and distal fixation holes 320, 322 and a saw slot 324. A window 326 allows access to a bone while the guide 300 is positioned on the bone. The proximal member 304 includes proximal fixation holes 328 and a saw slot 330. A window 332 allows access to a bone while the guide 300 is positioned on the bone.

Figure 28:
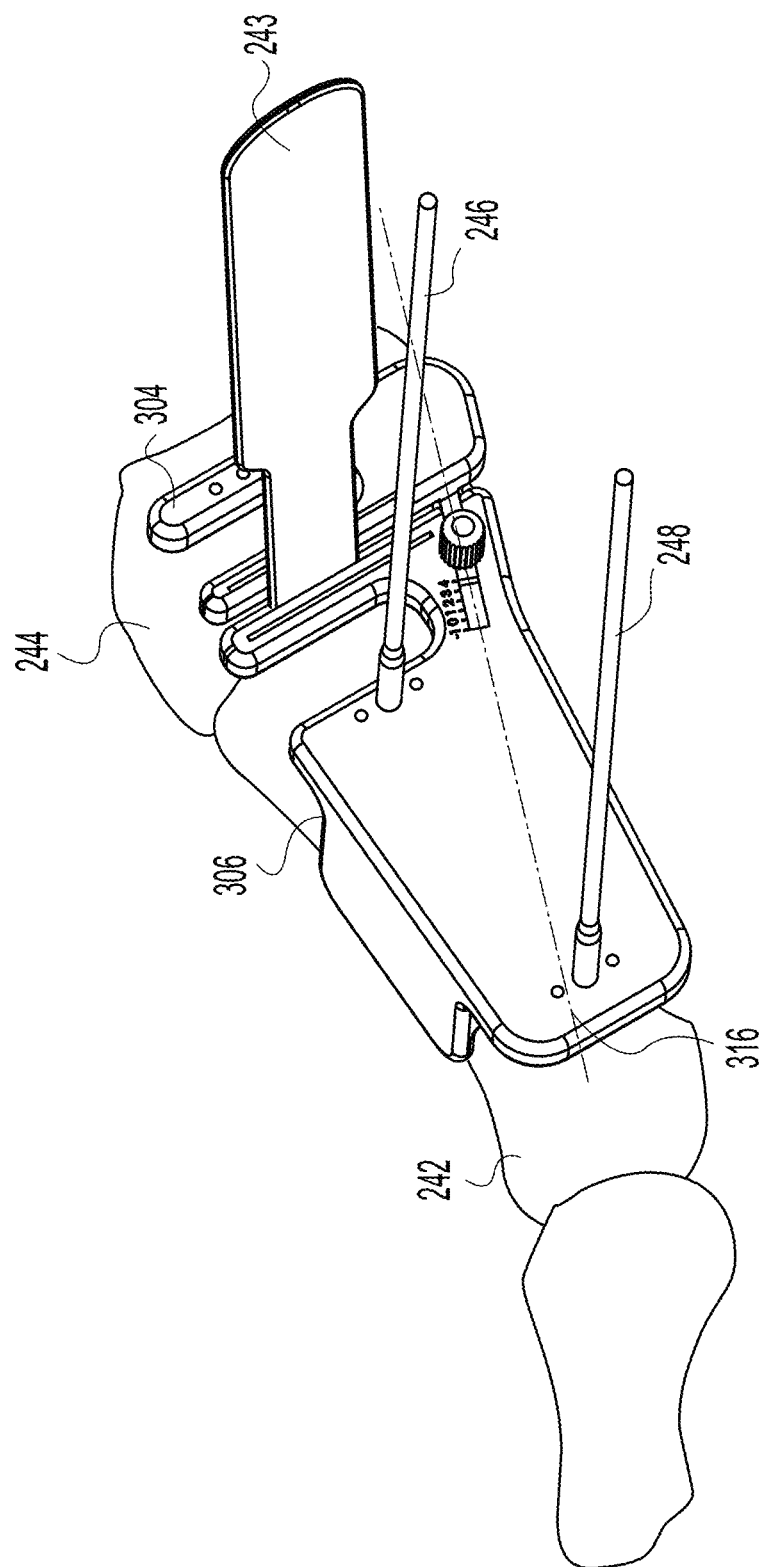
FIGS. 28-32 illustrate the use of the osteotomy guide of FIG. 26 to perform an osteotomy.

FIGS. 28-32 depict an illustrative method of performing an osteotomy using the guide 300 of FIG. 26. The proximal and distal members 304, 306 are positioned in a desired relative position, e.g. to set a desired cut spacing, and locked with the locking screw 340. In FIG. 28, the distal member is indexed to the metatarsus 242 as described above relative to the guide 200 of FIG. 14. A feeler gauge 243 is inserted between the proximal and distal members 304, 306 and used to align the guide 300 with the metatarsocuneiform joint 244. It may be necessary to loosen the locking screw 340 and adjust the relative position of the proximal and distal members to allow the gauge 243 to fit between the members. In addition, the motion axis 316 is aligned parallel to the floor as if the patient was standing. This will ensure that the relative loading of the rays of the foot is maintained after the first metatarsus is shortened as will be explained below. Pins 246, 248 are placed through the fixation holes 320, 322 to fix the distal member 306 to the metatarsus.

Figure 29:
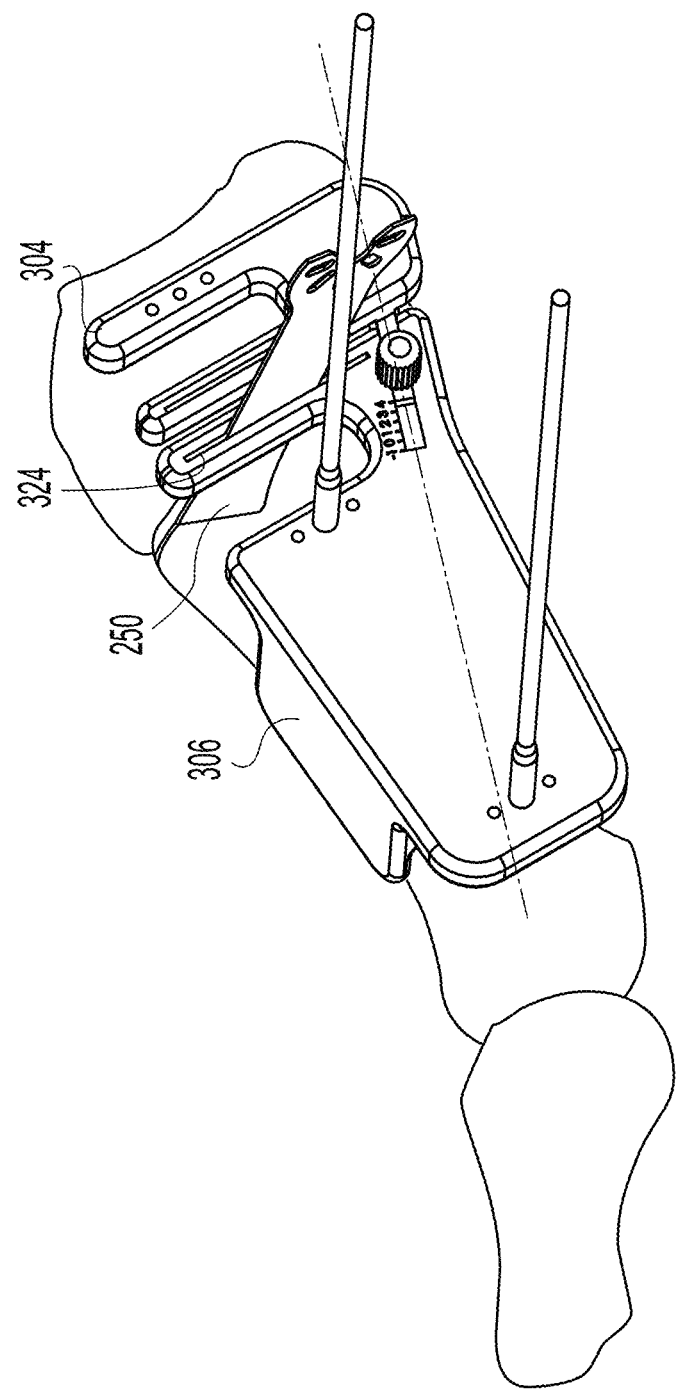

In FIG. 29, a saw blade 250 in a powered handpiece (not shown) is guided in the saw slot 324 of the distal member 306 to remove bone from the proximal end of the metatarsus. This creates the first planar cut surface 260 and gap 262 and increases the mobility between the metatarsus 242 and cuneiform 252 as described above relative to FIGS. 21-25.

Figure 30:
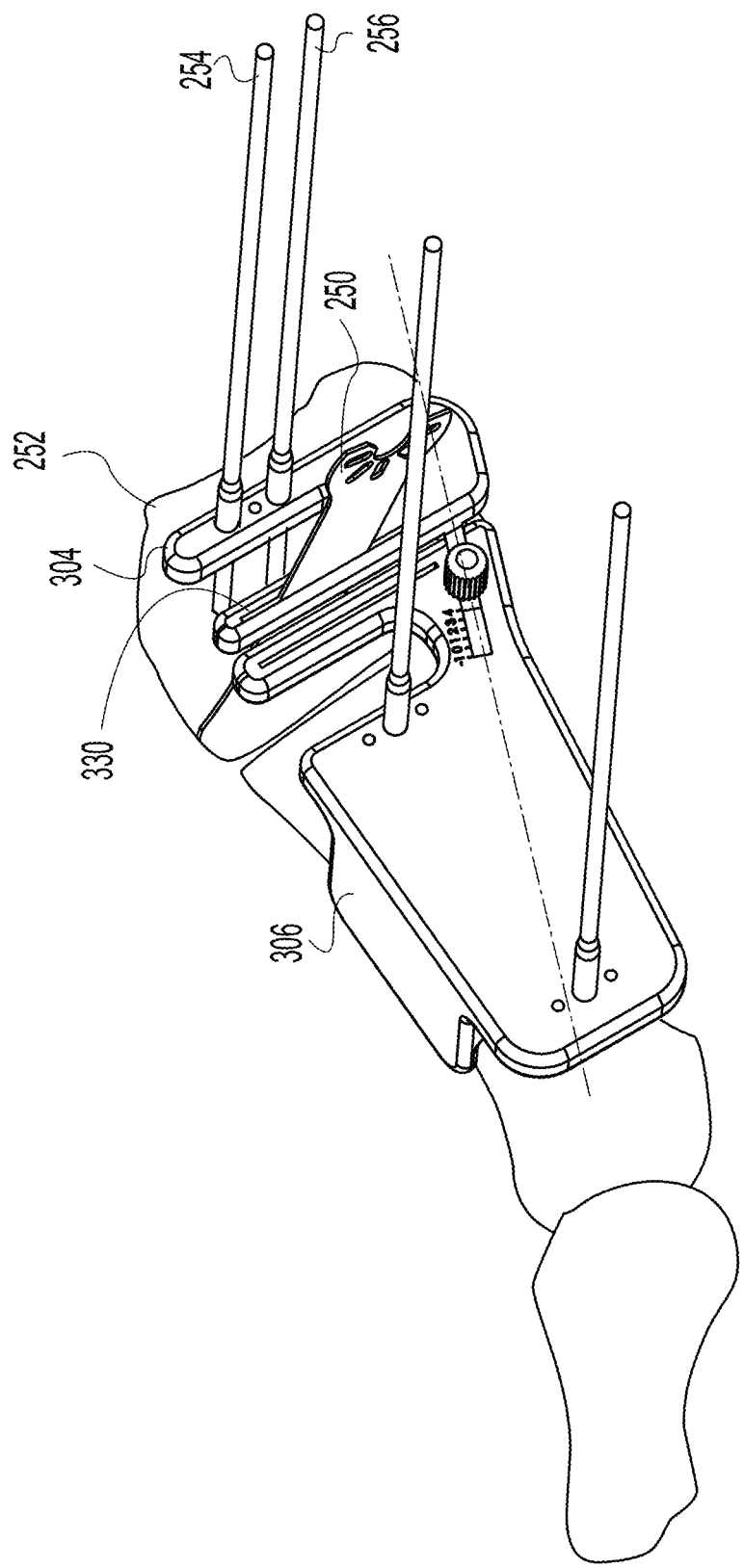

In FIG. 30, once the bones are oriented in a desired position and the proximal and distal members 304, 306 are locked in a desired relative position, pins 254, 256 are placed in the fixation holes 328 of the proximal member 304 to fix guide 300 to the cuneiform 252. A saw blade 250 is guided in the saw slot 330 of the proximal member 304 to remove bone from the distal end of the cuneiform 252. This creates the second planar cut surface 264 on the cuneiform 252 in predetermined relationship to the first planar cut surface 260 on the metatarsus 242 and the gap 266 as described above relative to FIGS. 21-25.

Figure 31:
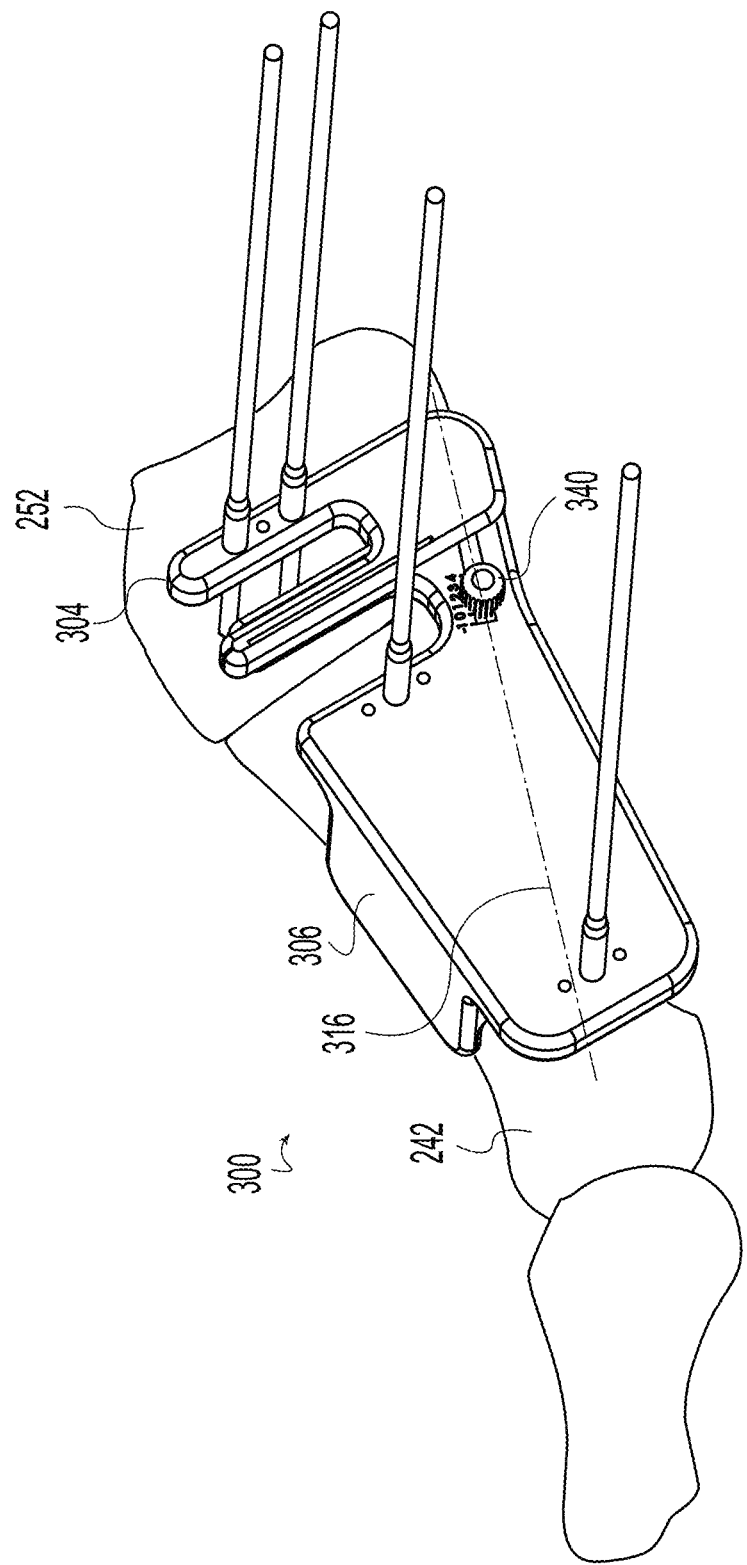
Figure 32:
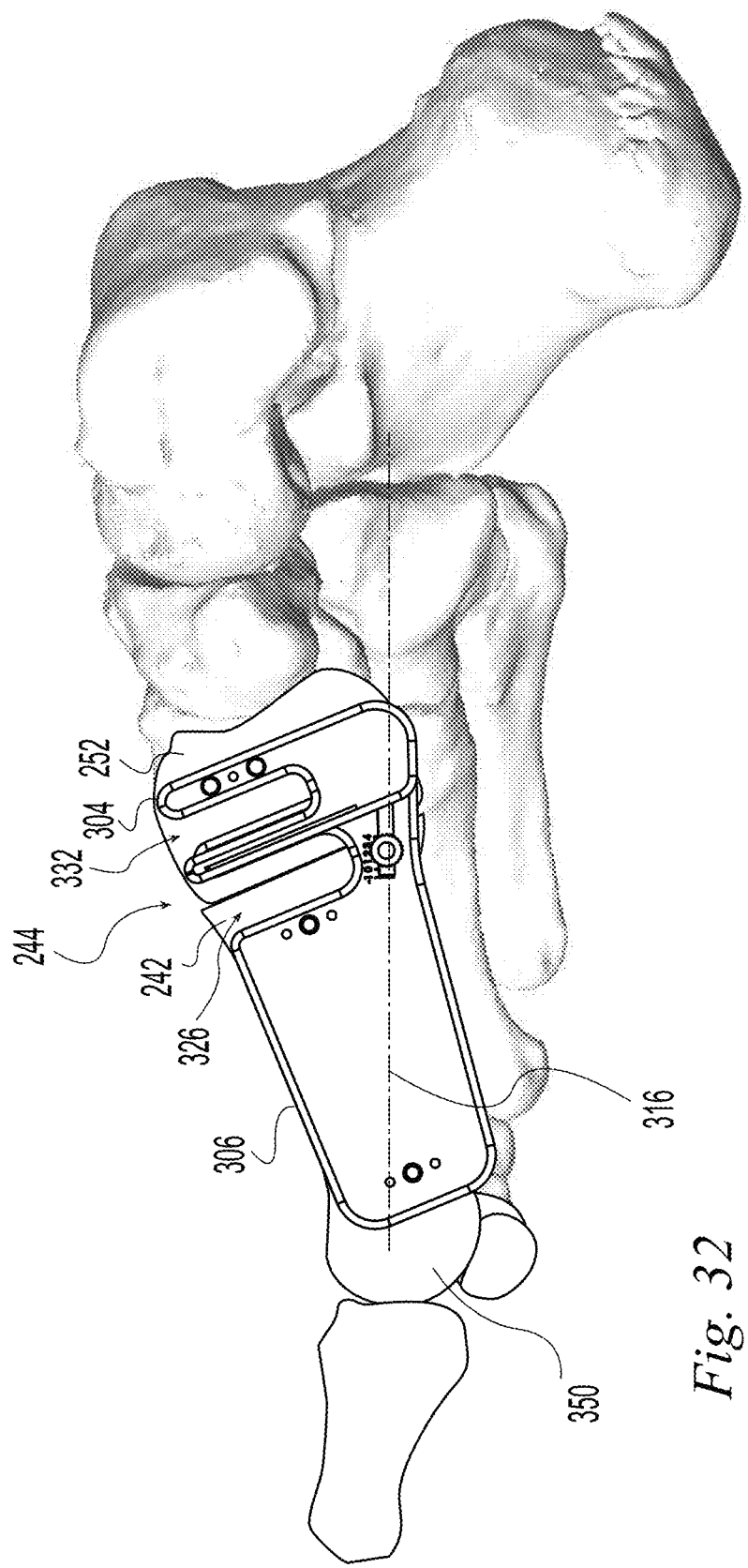

In FIG. 31, a controlled reduction of the metatarsus and cuneiform may be performed by loosening the locking screw 340 and translating the metatarsus 242 toward the cuneiform 252. Since the bones are fixed to the distal and proximal members 306, 304 of the guide 300 respectively, the metatarsus 242 is constrained to translate along a path parallel to the motion axis 316. As best seen in FIG. 32, the metatarsal heads are arranged in the standing foot to distribute body weight among the rays of the foot. If the vertical alignment of the metatarsal heads is altered, the weight distribution on the foot can change from the anatomic distribution and cause abnormal wear and pain. By translating the cut metatarsus 242 along the motion axis 316 that has been positioned parallel to the floor relative to the standing foot, the vertical alignment of the head 350 of the cut metatarsal 242 is maintained. The metatarsus 242 is translated until the cut surface of the metatarsus abuts the cut surface of the cuneiform. In the illustrative example of FIGS. 26-32, this will correspond to a reading of "0" on the guide 300. Further translation will result in compression of the bone surfaces together and negative readings on the guide 300. Reduction and/or compression may be facilitated by using a forceps or clamp, e.g. a towel clamp, to press the bone portions together. For example, a towel clamp may be engaged with the edges of the proximal and distal members 304, 306, inside the windows 326, 332, in unused fixation holes, on the fixation pins, or in features specifically added for that purpose. The locking screw 340 may be tightened to hold the bones in the reduced position while fixation such as one or more pins, plates, screws, rods or other suitable fixation is applied. The windows 326, 332 in the members 306, 304 permits access through the guide 300 to facilitate placing such fixation.

Figure 33:
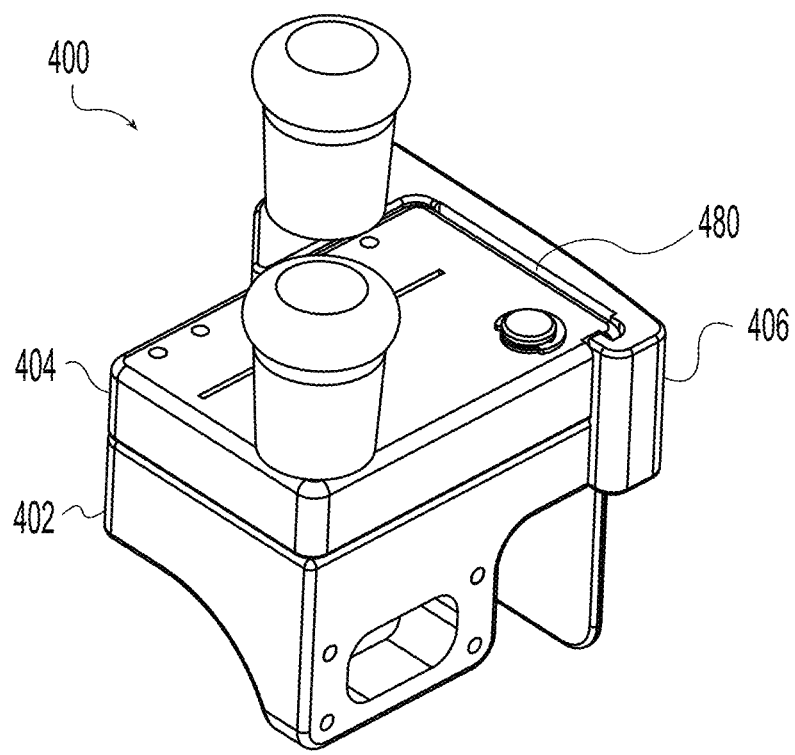
FIG. 33 is a perspective view of an osteotomy guide according to the present invention.
Figure 34:
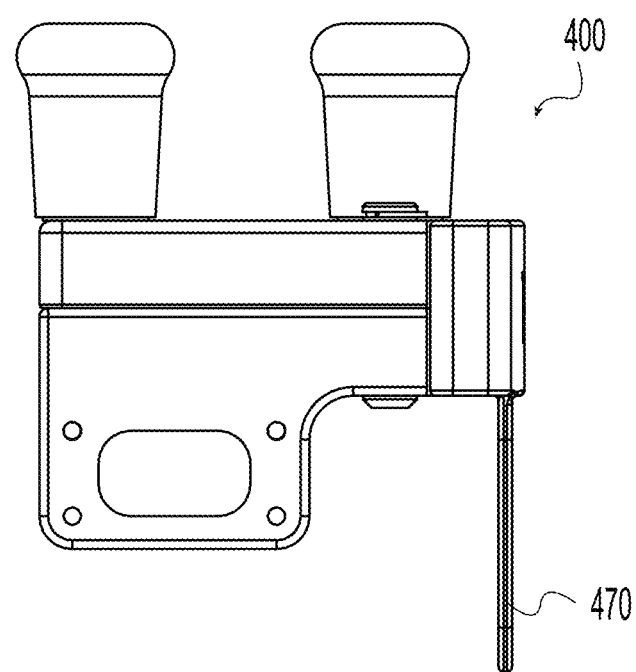
FIG. 34 is a front elevation view of the osteotomy guide of FIG. 33.
Figure 35:
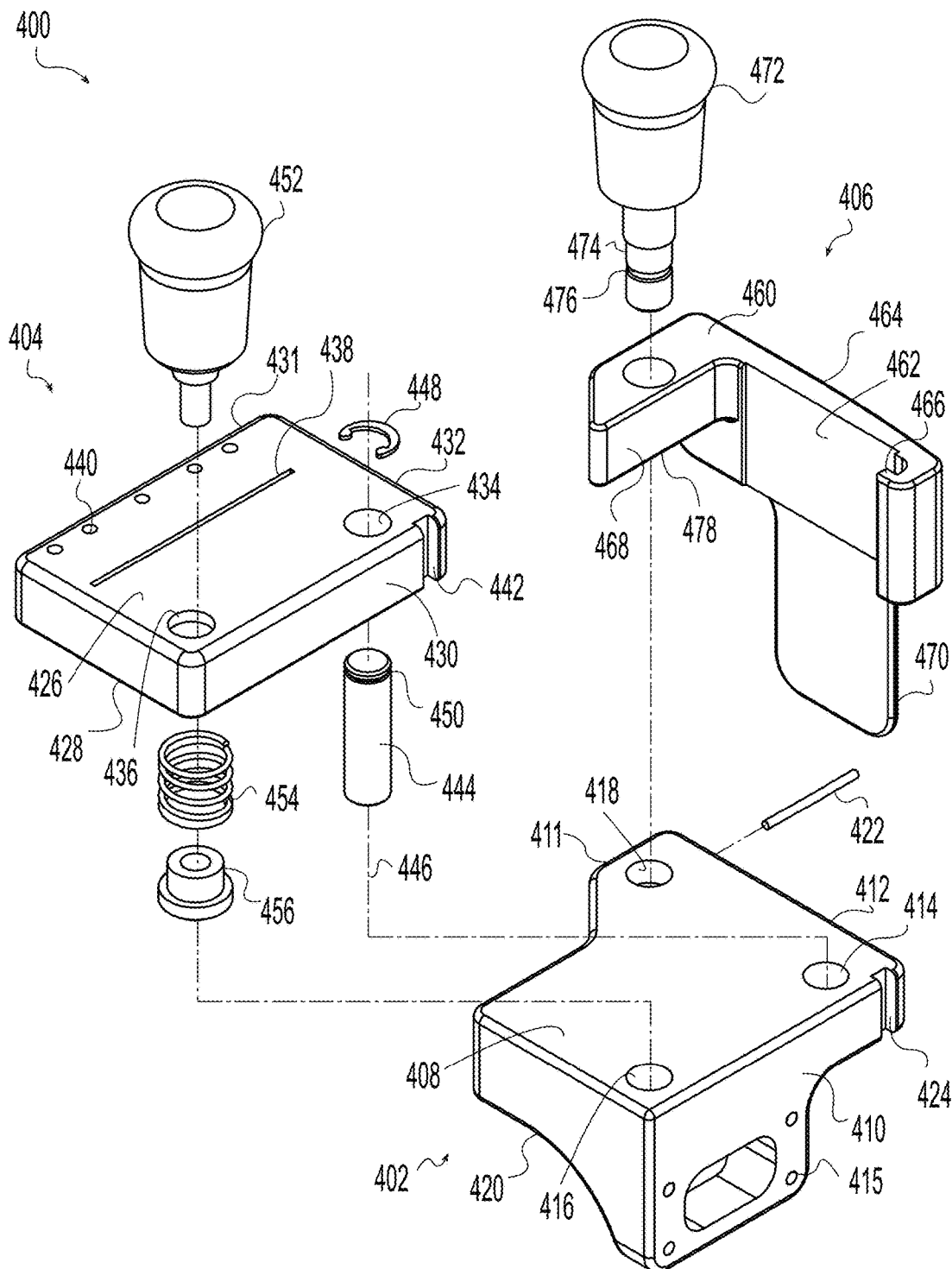
FIG. 35 is an exploded perspective view of the osteotomy guide of FIG. 33.

FIGS. 33-35 depict an illustrative osteotomy guide 400 according to the present invention. The guide 400 is similar to that of the previous examples. However, the guide 400 includes a guide body including a first member 402, a second member 404, and a third member 406. The first member 402 includes a top surface 408, a front surface 410, a back surface 411 opposite the front surface, and an end surface 412. The top surface 408 includes a pivot pin hole 414 and first and second rotation stop holes 416, 418 all of which extend at least partway through the first member 402 normal to the top surface 408. An indexing surface 420, opposite the top surface 408 may be positioned on a patient such as on the skin or directly on the bone. The front surface 410 includes fixation elements 415 in the form of through holes for receiving pins (not shown) to fix the first member 402 to the bone. A spring pin 422 is inserted into the first member so that it crosses a portion of the second rotation stop hole 418 (FIG. 39) and is operable to resiliently retain a pin inserted into the second rotation stop hole 418. A notch 424 is formed vertically (i.e. normal to the top surface 408) in the front surface and opens to the top surface 408.

The second member 404 includes a top surface 426, a bottom surface 428 opposite the top surface 426, a front surface 430, a back surface 431 opposite the front surface, and an end surface 432. The top surface 426 includes a pivot pin hole 434 and a locking pin hole 436 both of which extend through the second member 404 normal to the bottom surface 428. The locking pin hole 436 is enlarged in its lower portion toward the bottom surface 428. A guide slot 438 is formed through the second member 404 from the top surface to the bottom surface. The guide slot 438 may be used to guide a cutter such as a saw blade to cut an underlying bone. A plurality of fixation elements in the form of pin holes 440 are also formed through the second member 404 from the top surface 426. A notch 442 is formed vertically (i.e. normal to the bottom surface 428) in the front surface and opens to the top and bottom surfaces 426, 428. The second member 404 is mounted to the first member 402 with the bottom surface 428 of the second member 404 in contact with the top surface 408 of the first member 402 for rotation about a pivot pin 444 having a pivot pin axis 446. In the illustrative example of FIGS. 33-35, the pivot pin 444 is fixedly received in the pivot pin hole 414 of the first member 402. The pivot pin 444 may be secured by press fit, welding, pinning, staking, or similar operation. The pivot pin 444 is received in the pivot pin hole 434 of the second member 404 in rotating relationship. A clip 448 engages a groove 450 in the end of the pivot pin 444 that projects above the top surface 426 of the second member 404 to retain the second member 404 on the first member 402. A locking pin 452 engages the locking pin hole 436 of the second member and extends through the second member from the top surface 426 past the bottom surface 428. A spring 454 is trapped in the lower portion of the locking pin hole 436 by a spring retainer 456 secured to the locking pin 452. The end of the locking pin 452 extends through the spring retainer 456 and engages the first rotation stop hole 416 when the guide 400 is in the position shown in FIGS. 33-35. In the illustrative example of FIGS. 33-35, the locking pin 452 engages the first rotation stop hole 416 to secure the first and second members 402, 404 in a first operative position in which the end surfaces 412 and 432 are coplanar. The locking pin 452 may be partially withdrawn vertically from the first rotation stop hole 416 in opposition to the spring 454 to allow the second member to rotate about the pivot pin 444 to a second operative position in which it may be secured by allowing the spring 454 to bias the locking pin 452 into the second rotation stop hole 418. In the second operative position, the guide slot 438 is offset outwardly from the end surface 412 of the first member.

The end surfaces 412, 432 of the first and second members may be used to guide a cutter to cut bone to form a first cut when the guide 400 is in the first operative position. The guide slot 438 may be used to guide a cutter to cut bone to form a second cut offset from the first cut when the guide 400 is in the second operative position. The end surfaces 412, 432 and guide slot 438 may have any orientation relative to one another depending on the desired relationship of the first and second cuts. Preferably, they produce parallel cuts so that after the first cut an angular correction of the bone or joint may be made by the surgeon and confirmed by visualizing the new angle. When the second cut is made, parallel to the first cut, the cut surfaces may be brought together in planar contact so that they will heal together at the new angle. In the illustrative example of FIGS. 33-35, the end surfaces 412 and 432 are coplanar in the first operative position and define a plane for guiding a cutter. However in an alternative embodiment, the end surfaces 412, 432 need not be coplanar and only one of them may be used for a cutter guide. Alternatively, the end surfaces may not be used to define a cutter guide and another feature may be provided to guide the cutter in the first operative position.

The third member 406 includes a top surface 460, an inner side surface 462, and outer side surface 464, a tab 466 engageable with the notches 424, 442 of the first and second members, and an inner back surface 468 opposite the tab 466 and engageable with the back surfaces 411, 431 of the first and second members. A paddle 470 extends downwardly and is offset outwardly relative to the inner side surface 462 of the third member 406. A knob 472 is mounted to the third member such as by press fit, welding, pinning, staking or other operation and includes a post 474 with a groove 476 that projects below a bottom surface 478 of the third member 406 to engage the second rotational stop hole 418. The groove 476 engages the spring pin 422 to releasably retain the third member 406 on the first and second members 402, 404.

With the guide in the first operative position, the third member is engaged with the second and third members by sliding it downwardly to engage the tab 466 with the slots 424, 442 and the inner back surface 468 with the back surfaces 431, 411. The post 474 engages the second rotation stop hole 418 to releasably lock the third member 406 in place. The end surfaces 412, 432 of the first and second members and the inner side surface 462 of the third member define a guide slot 480 (FIG. 1) between them to guide a cutter. The third member is optional inasmuch as the end surfaces 412, 432 can be used alone for guiding a cutter however it is preferable to use the third member to provide additional constraint to guide the cutter. Optionally, the third member may be configured to guide a cutter without referencing the end surfaces 412, 432 such as by guiding the cutter solely on the inner side surface 462 or by providing the third member with a guide slot. Also with the guide in the first operative position and the third member engaged with the second and third members, the paddle 470 may be inserted into a joint between first and second bones such that guiding a cutter in the first operative position removes a portion of the first bone and removing the third member and guiding a cutter in the second operative position removes a portion of the second bone.

FIGS. 36-41 depict an illustrative method of performing an osteotomy using the guide 400 of FIGS. 33-35. In the illustrative example of FIGS. 36-41, the guide 400 is used to perform a fusion osteotomy of the MTC joint of a first ray of a human foot including a cuneiform 500, first metatarsus 502, and proximal phalanx 504.

In FIG. 36, the guide 400 is configured in the first operative position with the third member 406 attached. FIG. 37 is a top view of the guide 400 showing how it is configured for the step shown in FIG. 36. Due to the compact arrangement of the first operative position, visualization of the bones and alignment of the guide to the bones is simplified. The indexing surface 420 is placed in contact with the patient; e.g. on the skin over the metatarsus or directly in contact with the bone. In the example of FIGS. 36-41, the indexing surface 420 is placed on the dorsal portion of the foot with the top surface 426 of the second member facing dorsally and the front surfaces 410, 430 facing medially. The paddle 470 is placed in the MTC joint to position the guide 400 proximally/distally. With the guide 400 positioned on the first ray, fixation pins 490 may be inserted through the holes 415 in the first member and into the metatarsus 502 to secure the guide to the metatarsus 502. A cutter, e.g. saw blade 510, may then be guided in the guide slot 480 to form a cut 512 in the proximal metatarsus. The third member 406 is then removed by pulling upwardly on the knob 472.

In FIG. 38, with the guide in the first operative position and the third member 406 removed, the bone portion 514 freed by cutting the metatarsus 502 is easily withdrawn from the joint since no portion of the guide 400 overlies the bone portion 514. FIG. 39 is a top view of the guide 400 showing how it is configured for the step shown in FIG. 38. After the bone portion 514 is removed, the locking pin 452 is withdrawn and the second member 404 is pivoted about the pivot pin 444 to the second operative position as shown in FIG. 40.

In FIG. 40, the second member 404 has been pivoted to the second operative position and locked in place with the locking pin 452. FIG. 41 is a top view of the guide 400 showing how it is configured for the step shown in FIG. 40. With the bone portion 514 removed from the joint space, the metatarsus 502 and cuneiform 500 may be freely repositioned in one or more planes to place them in a new desired orientation. Once the bones are positioned, additional fixation pins 492 may be inserted through the pin holes 440 in the second member and into the cuneiform 500 to secure the bones and guide 400 in the new desired position. A cutter, e.g. saw blade 510, may then be guided in the guide slot 438 to form a cut 516 in the cuneiform 500 parallel to the cut 512 on the metatarsus 502. The guide 400 and the portion 518 of the cuneiform freed by the cut 516 may then be removed. The joint may then be reduced and secured for healing as described relative to the prior examples.

Various examples have been illustrated and described. The various examples may be substituted and combined and other alterations made within the scope of the invention.

What is claimed is:

1. A method of performing an osteotomy between a metatarsus and a cuneiform defining a metatarsocuneiform joint of a human foot, the method comprising:
   repositioning the metatarsus by rotating the metatarsus in one or more planes selected from a transverse plane, a coronal plane, and a sagittal plane;
   securing an osteotomy guide to at least one of the metatarsus and the cuneiform;
   cutting the metatarsus using a saw that is guided by a first guide slot in the osteotomy guide to form a metatarsus cut surface;
   cutting the cuneiform using a saw that is guided by a second guide slot in the osteotomy guide that is spaced apart from the first guide slot to form a cuneiform cut surface;
   removing the osteotomy guide;
   compressing the metatarsus and cuneiform to bring the metatarsus cut surface and the cuneiform cut surface together; and
   fixing the metatarsus and cuneiform together with one or more pins, plates, screws, or rods.

2. The method of claim 1, comprising rotating the metatarsus in each of the transverse plane, coronal plane, and sagittal plane.

3. The method of claim 1, wherein the osteotomy guide comprises a one-piece guide body comprising both the first and second guide slots.

4. The method of claim 1, wherein securing the osteotomy guide comprises inserting one or more pins through fixation holes in the osteotomy guide into the metatarsus or cuneiform.

5. The method of claim 1, comprising, after repositioning the metatarsus, inserting one or more pins through fixation holes in the osteotomy guide into the cuneiform.

6. The method of claim 1, wherein compressing the metatarsus and cuneiform comprises controlled reduction of the metatarsus and cuneiform using a compressor comprising a first member secured to the metatarsus and a second member secured to cuneiform, wherein the first and second members are engaged in a linear sliding relationship.

7. A method of performing an osteotomy between a metatarsus and a cuneiform defining a metatarsocuneiform joint of a human foot, the method comprising:
   positioning an osteotomy guide across the metatarsocuneiform joint, the osteotomy guide comprising a first cutting guide slot and a second cutting guide slot spaced apart from each other, wherein the first cutting guide slot and second cutting guide slot are angled relative to one another;
   securing the osteotomy guide to at least one of the metatarsus and the cuneiform;
   cutting the metatarsus using a saw that is guided by a first guide slot in the osteotomy guide to form a metatarsus cut surface;
   cutting the cuneiform using a saw that is guided by a second guide slot in the osteotomy guide that is spaced apart from the first guide slot to form a cuneiform cut surface;
   removing the osteotomy guide;
   compressing the metatarsus and cuneiform to bring the metatarsus cut surface and the cuneiform cut surface together; and fixing the metatarsus and cuneiform together with one or more pins, plates, screws, or rods.

8. The method of claim 7, wherein securing the osteotomy guide to the at least one of the metatarsus and the cuneiform comprises inserting one or more pins through one or more holes in the osteotomy guide and into the at least one of the metatarsus and the cuneiform.

9. The method of claim 7, comprising inserting a first pin through a first hole in the osteotomy guide into the metatarsal and inserting a second pin through a second hole in the osteotomy guide into the cuneiform.

10. The method of claim 7, wherein the osteotomy guide comprises a one-piece guide body comprising both the first and second guide slots.

11. The method of claim 7, wherein compressing the metatarsus and cuneiform comprises controlled reduction of the metatarsus and cuneiform using a compressor comprising a first member secured to the metatarsus and a second member secured to cuneiform, wherein the first and second members are engaged in a linear sliding relationship.

12. A method of performing an osteotomy between a metatarsus and a cuneiform defining a metatarsocuneiform joint of a human foot, the method comprising:

positioning an osteotomy guide across the metatarsocuneiform joint, the osteotomy guide comprising a joint alignment slot, a first cutting guide slot, and a second cutting guide slot, wherein each of the joint alignment slot, the first cutting guide slot, and the second cutting guide slot are spaced apart from each other, wherein positioning the osteotomy guide comprises positioning a joint-seeking paddle within the metatarsocuneiform joint and through the joint alignment slot;

securing the osteotomy guide to at least one of the metatarsus and the cuneiform;

cutting the metatarsus using a saw that is guided by a first guide slot in the osteotomy guide to form a metatarsus cut surface;

cutting the cuneiform using a saw that is guided by a second guide slot in the osteotomy guide that is spaced apart from the first guide slot to form a cuneiform cut surface;

removing the osteotomy guide;

compressing the metatarsus and cuneiform to bring the metatarsus cut surface and the cuneiform cut surface together; and fixing the metatarsus and cuneiform together with one or more pins, plates, screws, or rods.

13. The method of claim 12, wherein securing the osteotomy guide to the at least one of the metatarsus and the cuneiform comprises inserting one or more pins through one or more holes in the osteotomy guide and into the at least one of the metatarsus and the cuneiform.

14. The method of claim 12, comprising inserting a first pin through a first hole in the osteotomy guide into the metatarsal and inserting a second pin through a second hole in the osteotomy guide into the cuneiform.

15. The method of claim 12, wherein the osteotomy guide comprises a one-piece guide body comprising both the first and second guide slots.

16. The method of claim 12, wherein compressing the metatarsus and cuneiform comprises controlled reduction of the metatarsus and cuneiform using a compressor comprising a first member secured to the metatarsus and a second member secured to cuneiform, wherein the first and second members are engaged in a linear sliding relationship.

* * * * *